(12) United States Patent
Miyahara et al.

(10) Patent No.: US 6,344,435 B1
(45) Date of Patent: Feb. 5, 2002

(54) DETERGENT COMPOSITION

(75) Inventors: Reiji Miyahara; Koji Abe, both of Yokohama; Keiichi Uehara, Osaka; Toshio Fukuda; Takahiro Akutsu, both of Yokohama, all of (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/503,159

(22) Filed: Feb. 14, 2000

Related U.S. Application Data

(62) Division of application No. 09/095,047, filed on Jun. 10, 1998, now abandoned.

(51) Int. Cl.⁷ .......................... C11D 1/65; C07C 381/00

(52) U.S. Cl. .......................................... 510/494; 554/94

(58) Field of Search ................................ 510/494, 501, 510/491; 554/94

(56) References Cited

U.S. PATENT DOCUMENTS 3,454,500 A * 7/1969 Lancashire .................. 252/110
4,839,080 A * 6/1989 Jungermann et al. ....... 252/107

FOREIGN PATENT DOCUMENTS

| JP | 6-49500 | * | 2/1994 |
| WO | WO 96/08549 | * | 3/1996 |
| WO | WO 97/34475 | * | 9/1997 |

* cited by examiner

*Primary Examiner*—John Hardee
(74) *Attorney, Agent, or Firm*—Townsend & Banta

(57) ABSTRACT

The present invention is a detergent composition which contains alkali metal N-methyltaurate, alkali metal taurate or alkali metal hypotaurate salt of a specific organic acid or organic alkali N-methyltaurate, organic alkali taurate or organic alkali hypotaurate salt of a specific organic acid. The detergent composition of the present invention is an excellent detergent composition which has better foaming and foam quality, less pH dependence of the foaming, creamy foam, no creaking feeling or stretched feeling and no offensive odor.

6 Claims, 5 Drawing Sheets

DETERGENT COMPOSITION

CROSS REFERENCE TO A RELATED APPLICATIONS

This is a divisional application of application Ser. No. 09/095,047 filed Jun. 10, 1998 abandoned.

BACKGROUND OF THE INVENTION

1. Field of the Invention (1) The present invention relates to a detergent composition which contains an alkali metal N-methyltaurate salt or an organic alkali N-methyltaurate salt of a fatty acid.

(2) The present invention relates to a detergent composition which contains an alkali metal taurate salt or an organic alkali taurate salt of a fatty acid.

(3) The present invention relates to a detergent composition which contains an alkali metal hypotaurate salt or an organic alkali hypotaurate salt of a fatty acid.

(4) The present invention relates to a detergent composition which contains one or more types chosen from among an alkali metal taurate, N-methyltaurate or hypotaurate salt and an organic alkali taurate, N-methyltaurate or hypotaurate salt of a specific organic acid.

(5) The present invention relates to a detergent composition which contains one or more types chosen from among an alkali metal taurate, N-methyltaurate or hypotaurate salt and an organic alkali taurate, N-methyltaurate or hypotaurate salt of a acylated peptide.

2. The Prior Art

For the purpose of improving foaming and foam quality, soaps have been frequently used as detergents in products such as cleansing foam, body shampoo and shampoo. Of these, the most frequently used are soaps made from salts of alkali metals, such as sodium and potassium, with fatty acids. On the one hand, they have the advantages of a lower cost, good foaming and a creamy foam quality. On the other hand, they have shortcomings including poor foaming at a neutral pH, creaking feeling and a stretched feeling after use.

In order to address the foaming at a neutral pH and the creaking feeling, soaps made with a fatty acid and a weak base such as triethanol amine and lysine have been used. However, they have problems in that they have the amine odor due to the weak base part, the foam quality deteriorates and a refreshing feeling is harder to achieve, and they cannot be blended into solid products due to a lower dissolution point (Krafft point).

BRIEF SUMMARY OF THE INVENTION

The object of the present invention is to provide a detergent composition which has better foaming and foam quality, less pH dependence of the foaming, creamy foaming, no creaking feeling or stretched feeling and no offensive odor.

1. [Invention Described in Claims 1–4]

The inventors conducted earnest research based on the above mentioned problems and discovered that a detergent composition containing an alkali metal N-methyltaurate salt or an organic alkali N-methyltaurate salt of the fatty acid is superior to conventional products because it has better foaming and foam quality, less pH dependence of the foaming, creamy foam, no creaking feeling or stretched feeling and no offensive odor, thus completing the present invention.

That is, the present invention provides a detergent composition which contains an alkali metal N-methyltaurate salt of a fatty acid represented by the following general formula [Chemical formula 1].

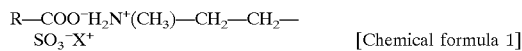
[Chemical formula 1]

(In this formula, R denotes a saturated or unsaturated hydrocarbon group with a carbon number of 7–23 and X denotes an alkali metal.)

Also, the present invention provides a detergent composition which contains an organic alkali N-methyltaurate salt of a fatty acid represented by the following general formula [Chemical formula 2].

[Chemical formula 2]

(In this formula, R denotes a saturated or unsaturated hydrocarbon group with a carbon number of 7–23 and Y denotes an organic alkali.)

Also, the present invention provides an alkali metal N-methyltaurate salt of a fatty acid represented by the following general formula [Chemical formula 3].

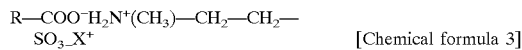
[Chemical formula 3]

(In this formula, R denotes a saturated or unsaturated hydrocarbon group with a carbon number of 7–23, and X denotes an alkali metal.)

Also, the present invention provides an organic alkali N-methyltaurate salt of a fatty acid represented by the following general formula [Chemical formula 4].

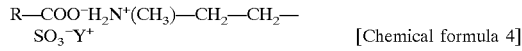
[Chemical formula 4]

(In this formula, R denotes a saturated or unsaturated hydrocarbon group with a carbon number of 7–23 and Y denotes an organic alkali.)

2. [Invention Described in Claims 5–8]

The inventors conducted earnest research based on the above mentioned problems and discovered that a detergent composition containing an alkali metal taurate salt or an organic alkali taurate salt of a fatty acid is superior to conventional products because it has better foaming and foam quality, less pH dependence of the foaming, creamy foam, no creaking feeling or stretched feeling and no offensive odor, thus completing the present invention.

That is, the present invention provides a detergent composition which contains an alkali metal taurate salt of a fatty acid represented by the following general formula [Chemical formula 5].

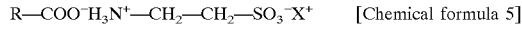
[Chemical formula 5]

(In this formula, R denotes a saturated or unsaturated hydrocarbon group with a carbon number of 7–23 and X denotes an alkali metal.)

Also, the present invention provides a detergent composition which contains an organic alkali taurate salt of a fatty acid represented by the following general formula [Chemical formula 6].

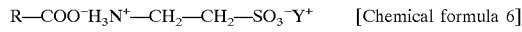
[Chemical formula 6]

(In this formula, R denotes a saturated or unsaturated hydrocarbon group with a carbon number of 7–23 and Y denotes an organic alkali.)

Also, the present invention provides a surfactant consisting of an alkali metal taurate salt of a fatty acid represented by the following general formula [Chemical formula 7].

$$R-COO^-H_3N^+-CH_2-CH_2-SO_3^-X^+ \quad \text{[Chemical formula 7]}$$

(In this formula, R denotes a saturated or unsaturated hydrocarbon group with a carbon number of 7–23, and X denotes an alkali metal.)

Also, the present invention provides a surfactant consisting of an organic alkali taurate salt of a fatty acid represented by the following general formula [Chemical formula 8].

$$R-COO^-H_2N^+-CH_2-CH_2-SO_3^-Y^+ \quad \text{[Chemical formula 8]}$$

(In this formula, R denotes a saturated or unsaturated hydrocarbon group with a carbon number of 7–23 and Y denotes an organic alkali.)

3. [Invention Described in Claims 9–12]

The inventors conducted earnest research based on the above mentioned problems and discovered that a detergent composition containing an alkali metal hypotaurate salt or an organic alkali hypotaurate salt of a fatty acid is superior to conventional products because it has better foaming and foam quality, less pH dependence of the foaming, creamy foam, no creaking feeling or stretched feeling and no offensive odor, thus completing the present invention.

That is, the present invention provides a detergent composition which contains an alkali metal hypotaurate salt of a fatty acid represented by the following general formula [Chemical formula 9].

$$R-COO^-H_2N^+-CH_2-CH_2-SO_3^-Y^+ \quad \text{[Chemical formula 9]}$$

(In this formula, R denotes a saturated or unsaturated hydrocarbon group with a carbon number of 7–23 and X denotes an alkali metal.)

Also, the present invention provides a detergent composition which contains an organic alkali hypotaurate salt of a fatty acid represented by the following general formula [Chemical formula 10].

$$R-COO^-H_2N^+-CH_2-CH_2-SO_3^-Y^+ \quad \text{[Chemical formula 10]}$$

(In this formula, R denotes a saturated or unsaturated hydrocarbon group with a carbon number of 7–23 and Y denotes an organic alkali.)

Also, the present invention provides a surfactant consisting of an alkali metal hypotaurate salt of a fatty acid represented by the following general formula [Chemical formula 11].

$$R-COO^-H_3N^+-CH_2-CH_2-SO_2^-X^+ \quad \text{[Chemical formula 11]}$$

(In this formula, R denotes a saturated or unsaturated hydrocarbon group with a carbon number of 7–23, and X denotes an alkali metal.)

Also, the present invention provides a surfactant consisting of an organic alkali hypotaurate salt of a fatty acid represented by the following general formula [Chemical formula 12].

$$R-COO^-H_3N^+-CH_2-CH_2-SO_2^-X^+ \quad \text{[Chemical formula 12]}$$

(In this formula, R denotes a saturated or unsaturated hydrocarbon group with a carbon number of 7–23 and Y denotes an organic alkali.)

4. [Invention Described in Claims 13–20]

The inventors conducted earnest research based on the above mentioned problems and discovered that a detergent composition containing one or more types chosen from among an alkali metal taurate, N-methyltaurate or hypotaurate salt and an organic alkali taurate, N-methyltaurate or hypotaurate salt of a specific organic acid is superior to conventional products because it has better foaming and foam quality, less pH dependence of the foaming, creamy foam, no creaking feeling or stretched feeling and no offensive odor, thus completing the present invention.

That is, the present invention provides a detergent composition which contains one or more types chosen from among an alkali metal taurate, N-methyltaurate or hypotaurate salt and an organic alkali taurate, N-methyltaurate or hypotaurate salt of an organic acid chosen from among a group consisting of hydroxy fatty acid, alkyl ether carboxylic acid, hydroxyalkyl ether carboxylic acid, acylated amino acid, glycerine ether carboxylic acid and ester carboxylic acid.

Also, the present invention provides a detergent composition which contains one or more types chosen from among an alkali metal taurate, N-methyltaurate or hypotaurate salt and an organic alkali taurate, N-methyltaurate or hypotaurate salt of hydroxy fatty acid represented by any of the following [Chemical formulas 13–14].

[Chemical formula 13]

$$(OH)_n-R^1-\underset{R^2}{COO^-H_2N^+}-CH_2-CH_2-SO_3^-X^+$$

(In this formula, $R^1$ denotes a saturated or unsaturated hydrocarbon group with a carbon number of 7–23, $R^2$ denotes a methyl group or hydrogen, X denotes an alkali metal or organic alkali and n denotes an integer 1–2.)

$$(OH)_n-R^1-COO^-H_3N^+-CH_2-CH_2-SO_2^-X^+ \quad \text{[Chemical formula 14]}$$

(In this formula, $R^1$ denotes a saturated or unsaturated hydrocarbon group with a carbon number of 7–23, X denotes an alkali metal or organic alkali and n denotes an integer 1–2.)

Also, the present invention provides a detergent composition which contains one or more types chosen from among an alkali metal taurate, N-methyltaurate or hypotaurate salt and an organic alkali taurate, N-methyltaurate or hypotaurate salt of alkyl ether carboxylic acid represented by any of the following [Chemical formulas 15–16].

[Chemical formula 15]

$$R^1-O(CH_2)_nCOO^-H_2N^+-\underset{R^2}{}-CH_2-CH_2-SO_3^-X^+$$

(In this formula, $R^1$ denotes a saturated or unsaturated hydrocarbon group with a carbon number of 8–24, $R^2$ denotes a methyl group or hydrogen, X denotes an alkali metal or organic alkali and n denotes an integer 1–2.)

$$R^1-O(CH_2)_nCOO^-H_3N^+-CH_2-CH_2-SO_2^-X^+ \quad \text{[Chemical formula 16]}$$

(In this formula, $R^1$ denotes a saturated or unsaturated hydrocarbon group with a carbon number of 8–24, $R^2$ denotes a methyl group or hydrogen, X denotes an alkali metal or organic alkali and n denotes an integer 1–2.)

Also, the present invention provides a detergent composition which contains one or more types chosen from among an alkali metal taurate, N-methyltaurate or hypotaurate salt and an organic alkali taurate, N-methyltaurate or hypotaurate salt of hydroxyalkyl ether carboxylic acid represented by any of the following [Chemical formulas 17–18].

[Chemical formula 17]

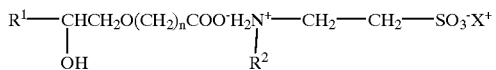

(In this formula, $R^1$ denotes a saturated or unsaturated hydrocarbon group with a carbon number of 6–22, $R^2$ denotes a methyl group or hydrogen, X denotes an alkali metal or organic alkali and n denotes an integer 1–2.)

[Chemical formula 18]

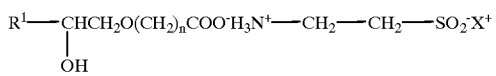

(In this formula, $R^1$ denotes a saturated or unsaturated hydrocarbon group with a carbon number of 8–24, X denotes an alkali metal or organic alkali and n denotes an integer 1–2.)

Also, the present invention provides a detergent composition which contains one or more types chosen from among an alkali metal taurate, N-methyltaurate or hypotaurate salt and an organic alkali taurate, N-methyltaurate or hypotaurate salt of acylated amino acid represented by any of the following [Chemical formulas 19–20].

[Chemical formula 19]

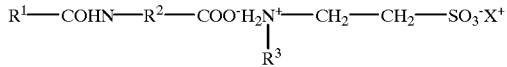

(In this formula, $R^1$ denotes a saturated or unsaturated hydrocarbon group with a carbon number of 7–23, $R^2$ denotes a residue of an amino acid with the amino group and the carboxyl group removed, $R^3$ denotes a methyl group or hydrogen, X denotes an alkali metal or organic alkali and n denotes an integer 1–2.)

[Chemical formula 20]

(In this formula, $R^1$ denotes a saturated or unsaturated hydrocarbon group with a carbon number of 6–22, $R^2$ denotes a residue of an amino acid with the amino group and the carboxyl group removed, X denotes an alkali metal or organic alkali and n denotes an integer 1–2.)

Also, the present invention provides a detergent composition which contains one or more types chosen from among an alkali metal taurate, N-methyltaurate or hypotaurate salt and an organic alkali taurate, N-methyltaurate or hypotaurate salt of glycerine ether carboxylic acid represented by any of the following [Chemical formulas 21–22].

[Chemical formula 21]

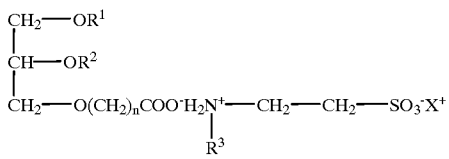

(In this formula, $R^1$ and $R^2$ denote a saturated or unsaturated hydrocarbon group with a carbon number of 8–24 or hydrogen, $R^3$ denotes a methyl group or hydrogen, X denotes an alkali metal or organic alkali and n denotes an integer 1–2.)

[Chemical formula 22]

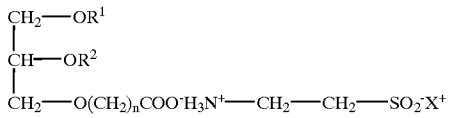

(In this formula, $R^1$ and $R^2$ denote a saturated or unsaturated hydrocarbon group with a carbon number of 8–24 or hydrogen, X denotes an alkali metal or organic alkali and n denotes an integer 1–2.)

Also, the present invention provides a detergent composition which contains one or more types chosen from among an alkali metal taurate, N-methyltaurate or hypotaurate salt and an organic alkali taurate, N-methyltaurate or hypotaurate salt of ester carboxylic acid represented by any of the following [Chemical formulas 23–24].

[Chemical formula 23]

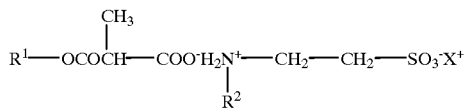

(In this formula, $R^1$ denotes a saturated or unsaturated hydrocarbon group with a carbon number of 7–23, $R^2$ denotes a methyl group or hydrogen and X denotes an alkali metal or organic alkali.)

[Chemical formula 24]

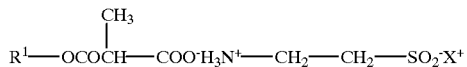

(In this formula, $R^1$ denotes a saturated or unsaturated hydrocarbon group with a carbon number of 7–23 and X denotes an alkali metal or organic alkali.)

Also, the present invention provides an alkali metal taurate, N-methyltaurate or hypotaurate salt or an organic alkali taurate, N-methyltaurate or hypotaurate salt of an organic acid chosen from among a group consisting of hydroxy fatty acid, alkyl ether carboxylic acid, hydroxyalkyl ether carboxylic acid, acylated amino acid, glycerine ether carboxylic acid and ester carboxylic acid, represented by the following [Chemical formulas 25–36].

[Chemical formula 25]

$$(OH)_n-R^1-COO^-H_2N^+(R^2)-CH_2-CH_2-SO_3^-X^+$$

(In this formula, $R^1$ denotes a saturated or unsaturated hydrocarbon group with a carbon number of 7–23, $R^2$ denotes a methyl group or hydrogen, X denotes an alkali metal or organic alkali and n denotes an integer 1–2.)

[Chemical formula 26]

$$(OH)_nR^1-COO^-H_3N^+-CH_2-CH_2-SO_2^-X^+$$

(In this formula, $R^1$ denotes a saturated or unsaturated hydrocarbon group with a carbon number of 7–23, X denotes an alkali metal or organic alkali and n denotes an integer 1–2.)

[Chemical formula 27]

$$R^1-O(CH_2)_nCOO^-H_2N^+(R^2)-CH_2-CH_2-SO_3^-X^+$$

(In this formula, $R^1$ denotes a saturated or unsaturated hydrocarbon group with a carbon number of 8–24, $R^2$ denotes a methyl group or hydrogen, X denotes an alkali metal or organic alkali and n denotes an integer 1–2.)

[Chemical formula 28]

$$(OH)_n-R^1-COO^-H_3N^+-CH_2-CH_2-SO_2^-X^+$$

(In this formula, $R^1$ denotes a saturated or unsaturated hydrocarbon group with a carbon number of 8–24, $R^2$ denotes a methyl group or hydrogen, X denotes an alkali metal or organic alkali and n denotes an integer 1–2.)

[Chemical formula 29]

$$R^1-CH(OH)CH_2O(CH_2)_nCOO^-H_2N^+(R^2)-CH_2-CH_2-SO_3^-X^+$$

(In this formula, $R^1$ denotes a saturated or unsaturated hydrocarbon group with a carbon number of 6–22, $R^2$ denotes a methyl group or hydrogen, X denotes an alkali metal or organic alkali and n denotes an integer 1–2.)

[Chemical formula 30]

$$R^1-CH(OH)CH_2O(CH_2)_nCOO^-H_3N^+-CH_2-CH_2-SO_2^-X^+$$

(In this formula, $R^1$ denotes a saturated or unsaturated hydrocarbon group with a carbon number of 8–24, X denotes an alkali metal or organic alkali and n denotes an integer 1–2.)

[Chemical formula 31]

$$R^1-COHN-R^2-COO^-H_2N^+(R^3)-CH_2-CH_2-SO_3^-X^+$$

(In this formula, $R^1$ denotes a saturated or unsaturated hydrocarbon group with a carbon number of 7–23, $R^2$ denotes a residue of an amino acid with the amino group and the carboxyl group removed, $R^3$ denotes a methyl group or hydrogen, X denotes an alkali metal or organic alkali and n denotes an integer 1–2.)

$$R^1-COHN-R^2-COO^-H_3N^+-CH_2-CH_2-SO_2^-X^+$$ [Chemical formula 32]

(In this formula, $R^1$ denotes a saturated or unsaturated hydrocarbon group with a carbon number of 6–22, $R^2$ denotes a residue of an amino acid with the amino group and the carboxyl group removed, X denotes an alkali metal or organic alkali and n denotes an integer 1–2.)

[Chemical formula 33]

$$\begin{array}{l} CH_2-OR^1 \\ CH-OR^2 \\ CH_2-O(CH_2)_nCOO^-H_2N^+(R^3)-CH_2-CH_2-SO_3^-X^+ \end{array}$$

(In this formula, $R^1$ and $R^2$ denote a saturated or unsaturated hydrocarbon group with a carbon number of 8–24 or hydrogen, $R^3$ denotes a methyl group or hydrogen, X denotes an alkali metal or organic alkali and n denotes an integer 1–2.)

[Chemical formula 34]

$$\begin{array}{l} CH_2-OR^1 \\ CH-OR^2 \\ CH_2-O(CH_2)_nCOO^-H_3N^+-CH_2-CH_2-SO_2^-X^+ \end{array}$$

(In this formula, $R^1$ and $R^2$ denote a saturated or unsaturated hydrocarbon group with a carbon number of 8–24 or hydrogen, X denotes an alkali metal or organic alkali and n denotes an integer 1–2.)

[Chemical formula 35]

$$R^1-OCOCH(CH_3)-COO^-H_2N^+(R^2)-CH_2-CH_2-SO_3^-X^+$$

(In this formula, $R^1$ denotes a saturated or unsaturated hydrocarbon group with a carbon number of 7–23, $R^2$ denotes a methyl group or hydrogen and X denotes an alkali metal or organic alkali.)

[Chemical formula 36]

$$R^1-OCOCH(CH_3)-COO^-H_3N^+-CH_2-CH_2-SO_2^-X^+$$

(In this formula, $R^1$ denotes a saturated or unsaturated hydrocarbon group with a carbon number of 7–23 and X denotes an alkali metal or organic alkali.)

5. [Invention Described in Claims 21–23]

The inventors conducted earnest research based on the above mentioned problems and discovered that a detergent composition containing one or more types chosen from among an alkali metal taurate, N-methyltaurate or hypotaurate salt and an organic alkali taurate, N-methyltaurate or hypotaurate salt of an acylated peptide is superior to conventional products because it has better foaming and foam quality, less pH dependence of the foaming, creamy foam, no creaking feeling or stretched feeling and no offensive odor, thus completing the present invention.

That is, the present invention provides a detergent composition which contains one or more types chosen from among an alkali metal taurate, N-methyltaurate or hypotaurate salt and an organic alkali taurate, N-methyltaurate or hypotaurate salt of an acylated peptide.

Also, the present invention provides a detergent composition which contains one or more types chosen from among an alkali metal taurate, N-methyltaurate or hypotaurate salt and an organic alkali taurate, N-methyltaurate or hypotaurate salt of an acylated peptide represented by the following [Chemical formulas 37–38].

[Chemical formula 37]

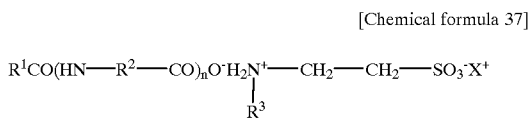

(In this formula, $R^1$ denotes a saturated or unsaturated hydrocarbon group with a carbon number of 7–23, $R^2$ denotes a residue of an amino acid with the amino group and the carboxyl group removed, $R^3$ denotes a methyl group or hydrogen, n denotes an integer 2–30, X denotes an alkali metal or organic alkali.)

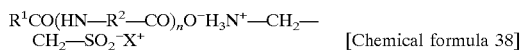

[Chemical formula 38]

(In this formula, $R^1$ denotes a saturated or unsaturated hydrocarbon group with a carbon number of 7–23, $R^2$ denotes a residue of an amino acid with the amino group and the carboxyl group removed, n denotes an integer 2–30, X denotes an alkali metal or organic alkali.)

Also, the present invention provides an alkali metal taurate, N-methyltaurate or hypotaurate salt or an organic alkali taurate, N-methyltaurate or hypotaurate salt of an acylated peptide represented by the following [Chemical formulas 39–40].

[Chemical formula 39]

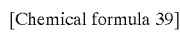

(In this formula, $R^1$ denotes a saturated or unsaturated hydrocarbon group with a carbon number of 7–23, $R^2$ denotes a residue of an amino acid with the amino group and the carboxyl group removed, $R^3$ denotes a methyl group or hydrogen, n denotes an integer 2–30, X denotes an alkali metal or organic alkali.)

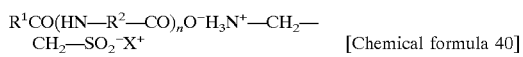

[Chemical formula 40]

(In this formula, $R^1$ denotes a saturated or unsaturated hydrocarbon group with a carbon number of 7–23, $R^2$ denotes a residue of an amino acid with the amino group and the carboxyl group removed, n denotes an integer 2–30, X denotes an alkali metal or organic alkali.)

DETAILED DESCRIPTION OF THE INVENTION

Figure 1:
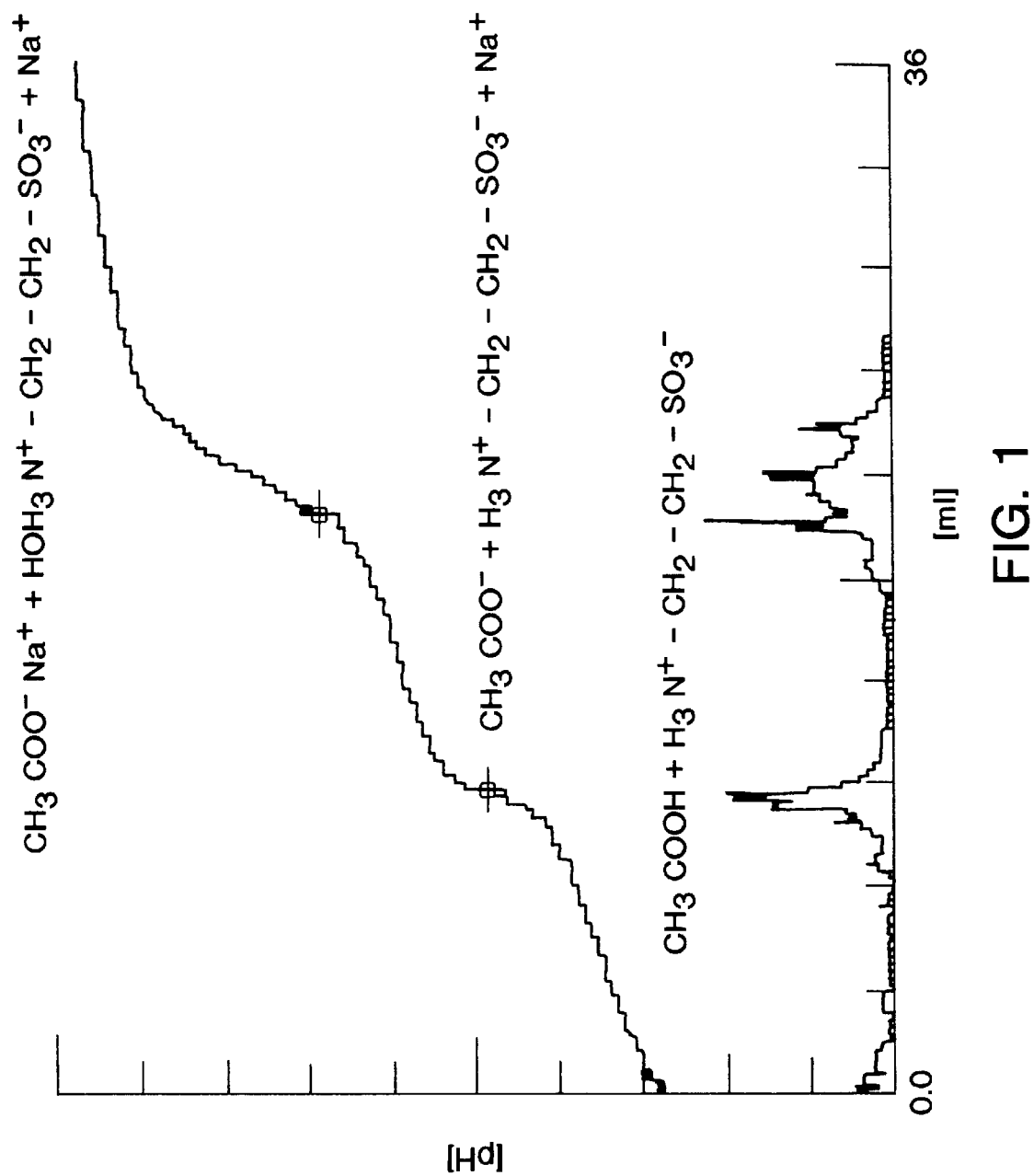
FIG. 1 is a neutralization titration curve obtained by neutralizing 100 ml of a mixture of 0.01 M acetate and 0.01 M taurine using an aqueous solution of 1 M sodium hydroxide.

The present invention is further described in detail below.

The detergent composition of the present invention refers to a composition which has a cleaning effect on objects. The range of objects to be cleaned is not limited. Preferably, it refers to a detergent used on human bodies, such as cosmetics and quasi-drugs. In addition to the aforementioned essential ingredients, other ingredients which are usually contained in a detergent composition can also be blended in, including anionic surfactants such as soap, a alkylsulfuric ester (salt), polyoxyethylenealkyl ether sulfuric acid (salt) and hydroxyalkyl ether carboxylic acid (salt), ampholytic surfactants such as imidazoline type ampholytic surfactants and betaine type ampholytic surfactants, non-ionic surfactants such as a polyoxyethylene alkyl ether, polyoxyethylene fatty acid ester, sucrose fatty acid ester, alkylglycoside and maltitolhydroxy aliphatic ether, cationic surfactants such as trimethylalkyl ammonium chloride, humectants such as glycerine, 1,3-butylene glycol and dipropylene glycol, extracts of plants such as Swertia japonica, Paeonia lactiflora, Iris florentina and Horsetail (Equisetum), drugs such as tranexamic acid and arbutin, perfumes and preservatives.

The detergent composition of the present invention has excellent foaming and foam quality, creamy foam, less pH dependence of the foaming, no creaking feeling or stretched feeling and no offensive odor.

1. [Invention Described in Claims 1–4, Claims 5–8, Claims 9–12]

In the aforementioned [Chemical formulas 1–12], R denotes a saturated or unsaturated hydrocarbon group with a carbon number of 7–23. Specific examples include linear saturated hydrocarbon groups such as a heptyl group, octyl group, nonyl group, decyl group, undecyl group, dodecyl group, tridecyl group, tetradecyl group, pentadecyl group, hexadecyl group, heptadecyl group, octadecyl group and tetraeicosyl group, branched saturated hydrocarbon groups such as a 2-methylheptadecyl group and 2-ethylpentyl group, linear unsaturated hydrocarbon groups such as a 8-heptadecenyl group, oleyl group and 4,6-octadecadienyl group, and branched unsaturated hydrocarbon groups such as a 2-methyloctadeca-6-ethenyl group.

In the aforementioned general formulas [Chemical formulas 1–12], X denotes an alkali metal such as sodium, potassium or lithium, and Y denotes an organic alkali such as triethanol amine, diethanol amine or lysine.

Preparation methods of the alkali metal N-methyltaurate salt of a fatty acid and organic alkali N-methyltaurate salt of a fatty acid represented by the aforementioned [Chemical formulas 1–4] include a method in which the fatty acid is dissolved at a temperature of approximately 80° C. and an aqueous solution of the alkali metal N-methyltaurate salt or the organic alkali N-methyltaurate salt is added to it while being stirred, or an aqueous solution of the N-methyltaurine and an aqueous solution of the alkali are separately added to it while being stirred.

Preparation methods of the alkali metal taurate salt of a fatty acid and organic alkali taurate salt of a fatty acid represented by the aforementioned [Chemical formulas 5–8] include a method in which the fatty acid is dissolved at a temperature of approximately 80° C. and an aqueous solution of the alkali metal taurate salt or the organic alkali taurate salt is added to it while being stirred, or an aqueous solution of the taurine and an aqueous solution of the alkali are separately added to it while being stirred.

Preparation methods of the alkali metal hypotaurate salt of a fatty acid and organic alkali taurate salt of a fatty acid represented by the aforementioned [Chemical formulas 9–12] include a method in which the fatty acid is dissolved at a temperature of approximately 80° C. and an aqueous solution of the alkali metal hypotaurate salt or the organic alkali hypotaurate salt is added to it while being stirred, or an aqueous solution of the taurine and an aqueous solution of the alkali are separately added to it while being stirred.

The appropriate blend ratio of the alkali metal N-methyltaurate salt or the organic alkali N-methyltaurate salt of fatty acid which is blended in the detergent composition of the present invention is 0.5–90 wt %.

The appropriate blend ratio of the alkali metal taurate salt or the organic alkali taurate salt of fatty acid which is blended in the detergent composition of the present invention is 0.5–90 wt %.

The appropriate blend ratio of the alkali metal, alkali earth metal or organic alkali hypotaurate salt of fatty acid which is blended in the detergent composition of the present invention is 0.5–90 wt %.

If the blend ratio is 0.5 wt % or less, then the effect of the present invention is hard to obtain. It is not preferable to have a blend ratio of more than 90 wt %, because then problems arise such as a reduction of the solubility in water.

2. [Invention Described in Claims 13–20]

In the aforementioned [Chemical formulas 13–36], specific examples of the saturated or unsaturated hydrocarbon group with a carbon number of 6–22, a carbon number of 7–23 or a carbon number of 8–24 include linear saturated hydrocarbon groups such as a hexyl group, heptyl group, octyl group, nonyl group, decyl group, undecyl group, dodecyl group, tridecyl group, tetradecyl group, pentadecyl group, hexadecyl group, heptadecyl group, octadecyl group and tetraeicosyl group, branched saturated hydrocarbon groups such as a 2-methylheptadecyl group and 2-ethylpentyl group, linear unsaturated hydrocarbon groups such as a 8-heptadecenyl group, oleyl group and 4,6-octadecadienyl group, and branched unsaturated hydrocarbon groups such as a 2-methyloctadeca-6-ethenyl group.

In the aforementioned [Chemical formulas 13–36], specific examples of alkali metal include sodium, potassium and lithium, and specific examples of the organic alkali include triethanol amine, diethanol amine and lysine.

Also, in the aforementioned [Chemical formulas 13–36], specific examples of the residue of amino acid with the amino group and the carboxyl group removed include residues of amino acids with the amino groups and the carboxyl groups removed from amino acids such as glycine, alanine, glutamic acid and sarcosine.

Preparation methods of the alkali metal taurate, N-methyltaurate or hypotaurate salt and an organic alkali taurate, N-methyltaurate or hypotaurate salt of various organic acids represented by the aforementioned [Chemical formulas 13–36] include a method in which the organic acid is dissolved under heated conditions and an aqueous solution of the alkali metal taurate, N-methyltaurate or hypotaurate or the organic alkali taurate, N-methyltaurate or hypotaurate is added to it while being stirred, or an aqueous solution of the taurine, N-methyltaurine or hypotaurine and an aqueous solution of the alkali are separately added to it while being stirred.

The appropriate blend ratio of the alkali metal taurate, N-methyltaurate or hypotaurate salt and an organic alkali taurate, N-methyltaurate or hypotaurate salt of the organic acid which is blended in the detergent composition of the present invention is 0.5–90 wt %. If the blend ratio is 0.5 wt % or less, then the effect of the present invention is hard to obtain. It is not preferable to have a blend ratio of more than 90 wt %, because then problems arise such as a reduction of the solubility in water.

3. [Invention Described in Claims 21–23]

In the aforementioned [Chemical formulas 37–40], R denotes a saturated or unsaturated hydrocarbon group with a carbon number of 7–23. Specific examples include linear saturated hydrocarbon groups such as a heptyl group, octyl group, nonyl group, decyl group, undecyl group, dodecyl group, tridecyl group, tetradecyl group, pentadecyl group, hexadecyl group, heptadecyl group, octadecyl group and tetraeicosyl group, branched saturated hydrocarbon groups such as a 2-methylheptadecyl group and 2-ethylpentyl group, linear unsaturated hydrocarbon groups such as a 8-heptadecenyl group, oleyl group and 4,6-octadecadienyl group, and branched unsaturated hydrocarbon groups such as a 2-methyloctadeca-6-ethenyl group.

Also, in the aforementioned [Chemical formulas 37–40], R2 denotes the residue of an amino acid with the amino group and the carboxyl group removed from amino acids which constitute peptides. Specific examples include residues of amino acids with the amino groups and the carboxyl groups removed which constitute hydrolyzed silk, hydrolyzed soybean protein, hydrolyzed collagen and hydrolyzed wheat protein, such as glycine, alanine, glutamic acid and sarcosine.

Also, in the aforementioned [Chemical formulas 37–40], specific examples of X include alkali metals such as sodium, potassium and lithium or organic alkalis including triethanolamine, diethanolamine and lysine.

Preparation methods of the alkali metal taurate, N-methyltaurate or hypotaurate salt and an organic alkali taurate, N-methyltaurate or hypotaurate salt of acylated peptide represented by the aforementioned [Chemical formulas 37–40] include a method in which the acylated peptide is dissolved under heated conditions and an aqueous solution of the alkali metal taurate, N-methyltaurate or hypotaurate or the organic alkali taurate, N-methyltaurate or hypotaurate is added to it while being stirred, or an aqueous solution of the taurine, N-methyltaurine or hypotaurine and an aqueous solution of the alkali are separately added to it while being stirred.

The alkali metal taurate, N-methyltaurate or hypotaurate salt and an organic alkali taurate, N-methyltaurate or hypotaurate salt of the acylated peptide which is blended in the detergent composition of the present invention is either blended singly or in combinations of two or more. The appropriate blend ratio of is 0.5–90 wt %. If the blend ratio is 0.5 wt % or less, then the effect of the present invention is hard to obtain. It is not preferable to have a blend ratio of more than 90 wt %, because then problems arise such as a reduction of the solubility in water.

EXAMPLES

The present invention is further described in detail below. The present invention is not limited to these examples.

1. Examples of Claims 1–4

Preparation Example 1
Preparation of Sodium N-methyltaurate Laurate 200 g of lauric acid was stirred and dissolved at 80° C. 278 ml of 50% aqueous solution of N-methyltaurine, 80 ml of 50% aqueous solution of sodium hydroxide and 200 ml of ion exchanged water were added to it and the mixture was stirred. After cooling, the product was taken out from the container and used as the 50% sodium N-methyltaurate laurate soap.

Preparation Example 2
Preparation of Triethanolamine N-methyltaurate Laurate 200 g of lauric acid was stirred and dissolved at 80° C. 278 ml of 50% aqueous solution of N-methyltaurine, 250 ml of 50% aqueous solution of triethanolamine and 200 ml of ion exchanged water were added to it and the mixture was stirred. After cooling, the product was taken out from the container and used as the original 50% triethanolamine N-methyltaurate laurate soap.

The alkali metal N-methyltaurate salt and the organic alkali N-methyltaurate salt of lauric acid thus prepared were used as test samples for the following tests to prove their efficacy.

[Foaming Test with the Shaking Method]

0.5 wt % of each sample in Table 1 was dissolved in ion exchanged water with 70 ppm calcium chloride already dissolved in it. The pH was then adjusted to 7.0. This solution was kept at 30° C., put into a Nessler's tube with an inner diameter of 3 cm and a height of 20 cm equipped with a sliding plug, and then tilted 90 degrees every second using a pendulum type shaker. After one minute, the sample was taken out of the shaker and the foam height, the foam film thickness and the foam density were measured. The time required for the foam height to be reduced to a half of the original height was also measured. The foam film thickness was measured by taking a photograph of the foam using a microscope at 100 times magnification and calculating the average value on the photograph. The foam density was obtained by sampling 10 ml of the foam and measuring its weight. The measurement results are shown in Table 2.

TABLE 1

| Sample name | Sample No. |
| --- | --- |
| Sodium N-methyltaurate laurate | Test sample 1 |
| Triethanolamine N-methyltaurate laurate | Test sample 2 |
| Sodium laurate | Control sample 3 |
| Potassium laurate | Control sample 4 |
| Magnesium laurate | Control sample 5 |
| Triethanolamine laurate | Control sample 6 |
| Lysine laurate | Control sample 7 |

TABLE 2

| Sample No. | Foam height (cm) | Foam film thickness ($\mu$) | Foam density (g/ml) | Duration (min.) |
| --- | --- | --- | --- | --- |
| Test sample 1 | 11.6 | 120 | 0.243 | 780 |
| Test sample 2 | 10.6 | 110 | 0.233 | 970 |
| Control sample 1 | 6.5 | 100 | 0.210 | 80 |
| Control sample 2 | 5.5 | 95 | 0.200 | 70 |
| Control sample 3 | 4.7 | 60 | 0.123 | 100 |
| Control sample 4 | 9.0 | 95 | 0.207 | 530 |

In the aforementioned foaming test with the shaking method, the foam height relates to how good the foaming is, the foam film thickness and the foam density relate to the creaminess of the foam, and the duration relates to the durability of the foam at the time of use. A larger value indicates a better performance. As shown in the table, sodium laurate, potassium laurate and magnesium laurate are harder to foam at pH 7 because they are salts of a weak acid and a strong base. On the other hand, the alkali metal N-methyltaurate salt of a fatty acid and the organic alkali N-methyltaurate salt of a fatty acid, which are the surfactants used in the present invention, as well as triethanolamine or a lysine salt of a fatty acid foam well at a more acidic pH because they are salts of a weak acid and a weak base. However, triethanolamine laurate and lysine laurate have lower Krafft points and are liquid at room temperature. Therefore they cannot be used for detergents with a solid formulation. Also, the detergent compositions of the present invention are also shown to be superior in terms of the creaminess and durability of the foam. These results indicate that the test samples, the alkali metal N-methyltaurate salt of a fatty acid and the organic alkali N-methyltaurate salt of a fatty acid, are compounds which have superior effects as surfactants.

[Sensory Test of the Odor]

A sensory test of the odor was conducted for the aforementioned test samples and control samples. The results are shown in Table 3.

TABLE 3

| Sample No. | Odor |
| --- | --- |
| Test sample 1 | No odor |
| Test sample 2 | No odor |
| Control sample 1 | No odor |
| Control sample 2 | No odor |
| Control sample 3 | No odor |
| Control sample 4 | Ammonia-like odor |
| Control sample 5 | Ammonia-like odor |

As shown above, the alkali metal N-methyltaurate salt of a fatty acid and the organic alkali N-methyltaurate salt of a fatty acid, which are the surfactants used in the present invention, are salts of a fatty acid and a weak base and yet, similar to alkali metal salts or alkali earth metal salts of a fatty acid, they don't have an offensive odor. This is believed to be due to the fact that they, unlike triethanolamine or lysine, have sulfonate, which is a strong acid, in the same molecule and therefore do not evaporate easily.

[Sensory Test of Actual Use]

Fifty panelists were used to conduct the actual use test for Test samples 1 and 2 as well as Control samples 1–5 shown in Table 1. The test was conducted as follows. 5 ml of a 10% aqueous solution of each sample was put on a hand and the hand was washed for 30 seconds. The feeling during use and after rinsing was rated with a five point scale based on the criteria shown in Table 4. The average of the fifty panelists was calculated to obtain the total evalution. The results are shown in Table 5.

TABLE 4

| Item | Evaluation point | | | | |
|---|---|---|---|---|---|
| | 5 | 4 | 3 | 2 | 1 |
| Foaming | Very good | Somewhat good | Normal | Somewhat poor | Very poor |
| Creaminess of the foam | Very good | Somewhat good | Normal | Somewhat poor | Very poor |
| Refreshing feeling after use | Very refreshing | Somewhat refreshing | Normal | Somewhat slimy | Very slimy |
| Moist feeling after drying | Very moist | Somewhat moist | Normal | Somewhat stretched | Very stretched |

⊚: The average of the evaluation points is 4–5.
o: The average of the evaluation points is 3–3.9.
Δ: The average of the evaluation points is 2–2.9.
x: The average of the evaluation points is 1–1.9.

TABLE 5

| Sample No. | Foaming | Creaminess of the foam | Refreshing feeling after use | Moist feeling after drying |
|---|---|---|---|---|
| Test sample 1 | ⊚ | ⊚ | ⊚ | ⊚ |
| Test sample 2 | ⊚ | ⊚ | o | ⊚ |
| Control sample 1 | ⊚ | o | ⊚ | x |
| Control sample 2 | o | Δ | o | x |
| Control sample 3 | ⊚ | o | Δ | Δ |
| Control sample 4 | o | o | x | ⊚ |
| Control sample 5 | o | ⊚ | Δ | o |

Comparison between samples in Table 5 with the same alkali portion indicates that insertion of N-methyltaurine in the structure improves all the feelings during use. The reason why an amphoteric compound which has both strong acid and weak base (—$NH_2$) functional groups, such as N-methyltaurine, has the aforementioned effects is believed to be as follows: during washing when there is plenty of water, the —$COO^-$ group of the fatty acid dissociates to give a feeling close to sodium soap, whereas after use when it is dry and there is not much water, the —$COO^-$ group of the fatty acid forms an ion pair with the $N^+$ portion of N-methyltaurine and the melting point of the hydrated crystal, dependent on the concentration, rises to cause insolubility in water and produce the feeling of use of sulfonic acid type surfactants.

[Structural Analysis Using the Neutralization Titration Curve]

For the purpose of determining the structure of an alkali metal N-methyltaurate salt of a fatty acid around neutral pH, (1) an aqueous solution of 0.1 M sodium hydroxide was dripped on 100 ml of a mixture of 0.01 M acetic acid and 0.01 M taurine to obtain a neutralization titration curve of this model compound, and (2) 0.01% of lauric acid was dissolved in 100 ml of an aqueous solution of 40% ethanol and 0.1% sodium N-methyltaurate was used to carry out a neutralization titration. The results of (1) and (2) are shown in FIG. 1 and FIG. 2, respectively.

In FIG. 1, the titration curve has 2 stages and this indicates that —$SO_3^-$ is neutralized first and then —$COO^-$ is neutralized. There is a buffer zone in the pH range 6–8 and the solute takes the form of $CH_3COO^-H_3N^+(CH_2)_2SO_3^-Na^+$ in this range.

Figure 2:
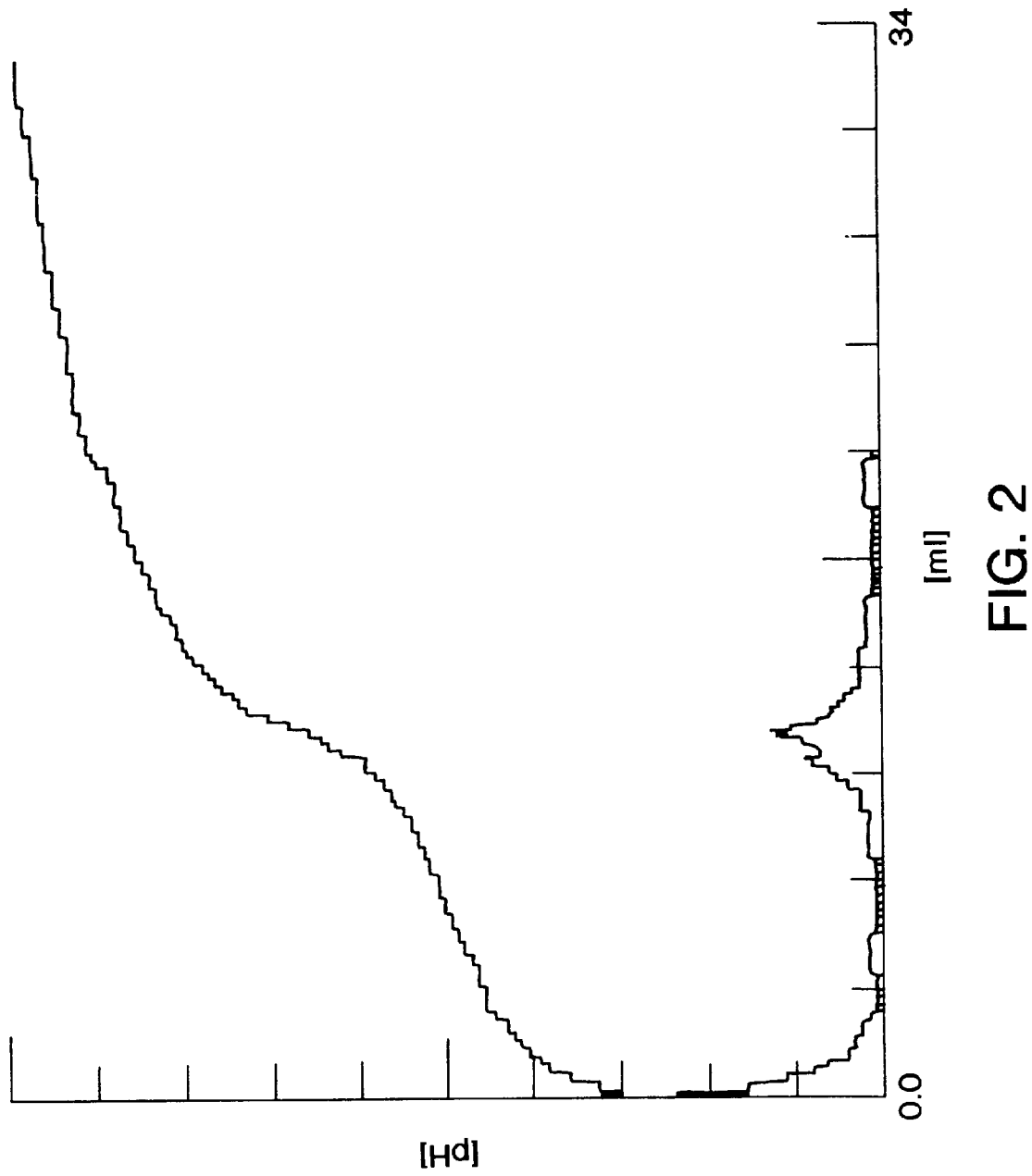
FIG. 2 is a neutralization titration curve obtained by neutralizing. 0.01% lauric acid using 0.01% sodium N-methyltaurate.

In FIG. 2, the titration curve is more gradual, indicating neutralization between the weak acid and weak base. Considering this and the aforementioned result, the structure of the test sample in the pH range of 6–8 is estimated to be R—$COO^-H_2N^+$—$(CH_3)(CH_2)_2SO_3^-Na^+$.

[$^{13}$C-NMR Structural Analysis of a Sodium N-methyltaurate Salt of Lauric Acid]

Figure 3:
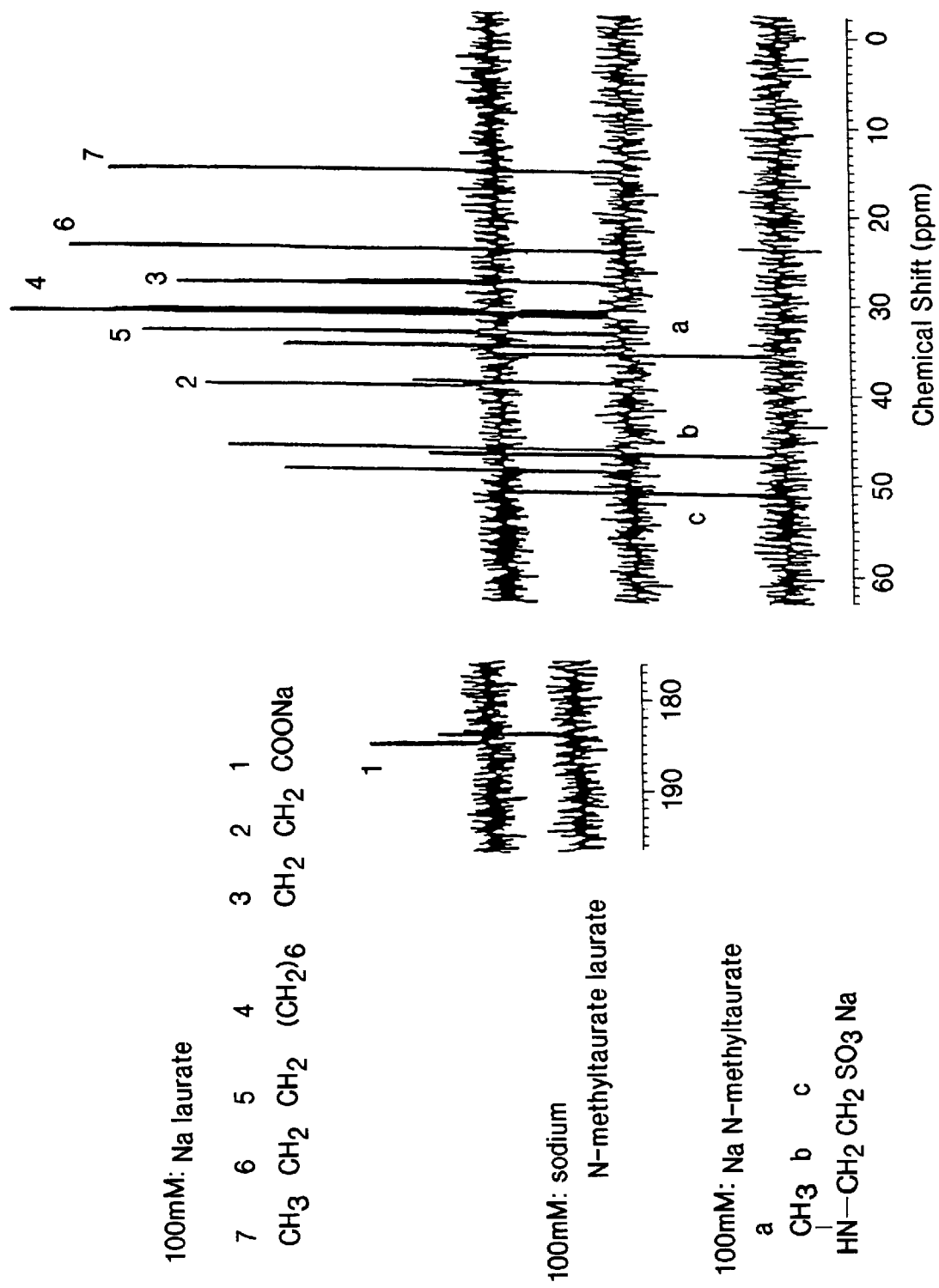
FIG. 3 is $^{13}$C-NMR spectra showing a comparison between Na laurate, sodium N-methyltaurate laurate and Na N-methyltaurate.

Heavy water solutions of 100 mM sodium laurate, sodium N-methyltaurate and sodium N-methyltaurate laurate were prepared and $^{13}$C-NMR measurement was conducted on each of them. The spectra are shown in FIG. 3. In the comparison between sodium N-methyltaurate and sodium N-methyltaurate laurate, the carbon at the β position in relation to the nitrogen had a −2.58 ppm shift to a higher magnetic field. This indicates that the nitrogen portion of sodium N-methyltaurate is positively ionized. In the comparison between sodium N-methyltaurate laurate and sodium laurate, the —$COO^-$ group had a −0.85 ppm shift and the carbons at the α position and the β position had −0.45 ppm and 0.14 ppm shifts, respectively, to a higher magnetic field. This indicates that the carbon atom of the carboxyl group is subjected to the shielding effect, suggesting that the (−) charge of the carboxylic acid is reduced and the $RCOO^-H_2N^+$— portion is close to the state of an ion pair rather than complete dissociation. Therefore, the reason why the detergent composition of the present invention feels moist when dried is believed to be as follows: when there is less water, the —$COO^-$ group of the fatty acid and the $N^+$ portion of the N-methyltaurine form an ion pair and produce the feeling of use of that of a sulfonic acid type surfactant.

[Measurement of the Krafft Point of Sodium N-methyltaurate Laurate]

Figure 4:
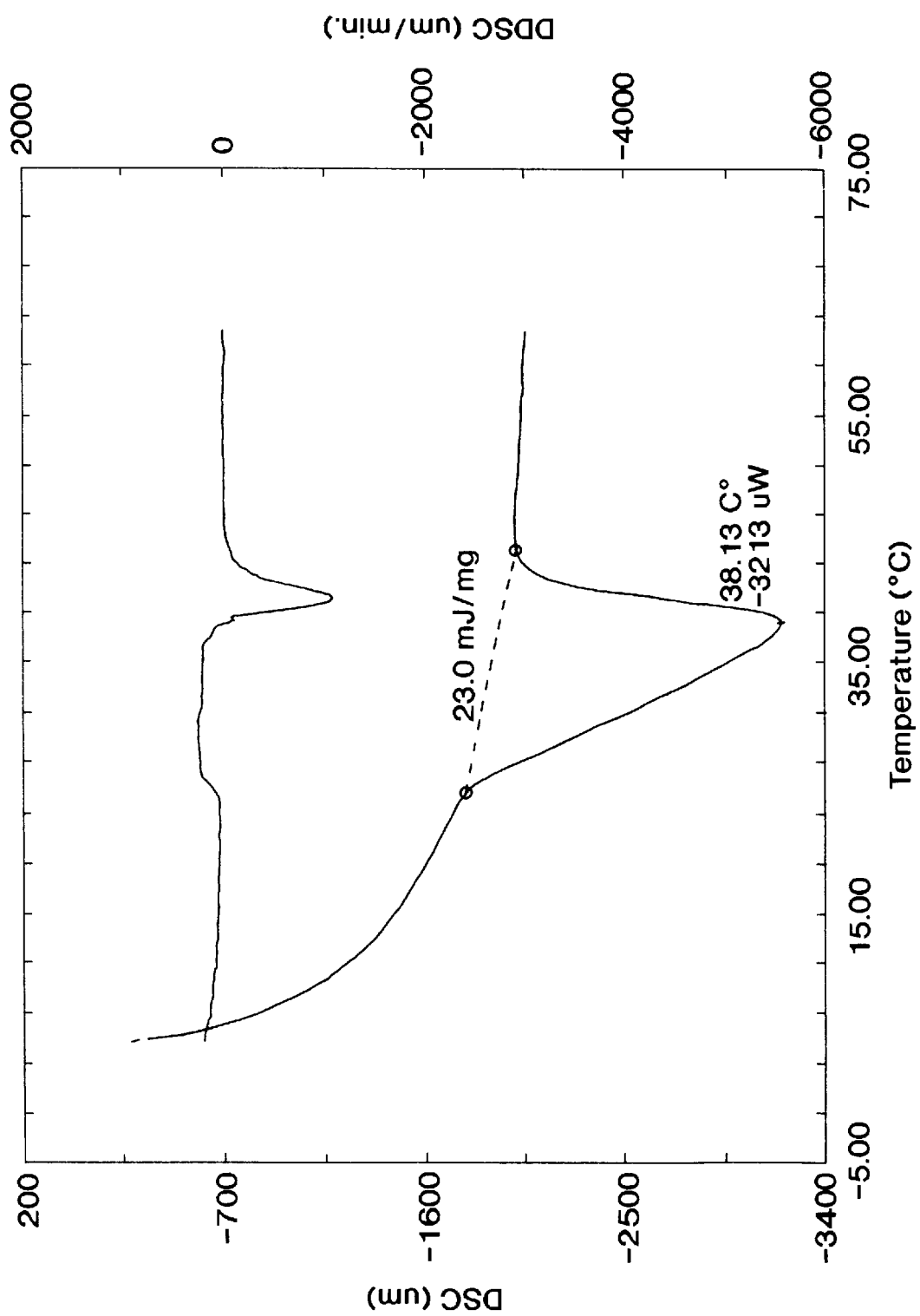
FIG. 4 is a measurement curve obtained with a differential canning calorimeter to determine the Krafft point of an aqueous solution of 30% sodium N-methyltaurate laurate.
Figure 5:
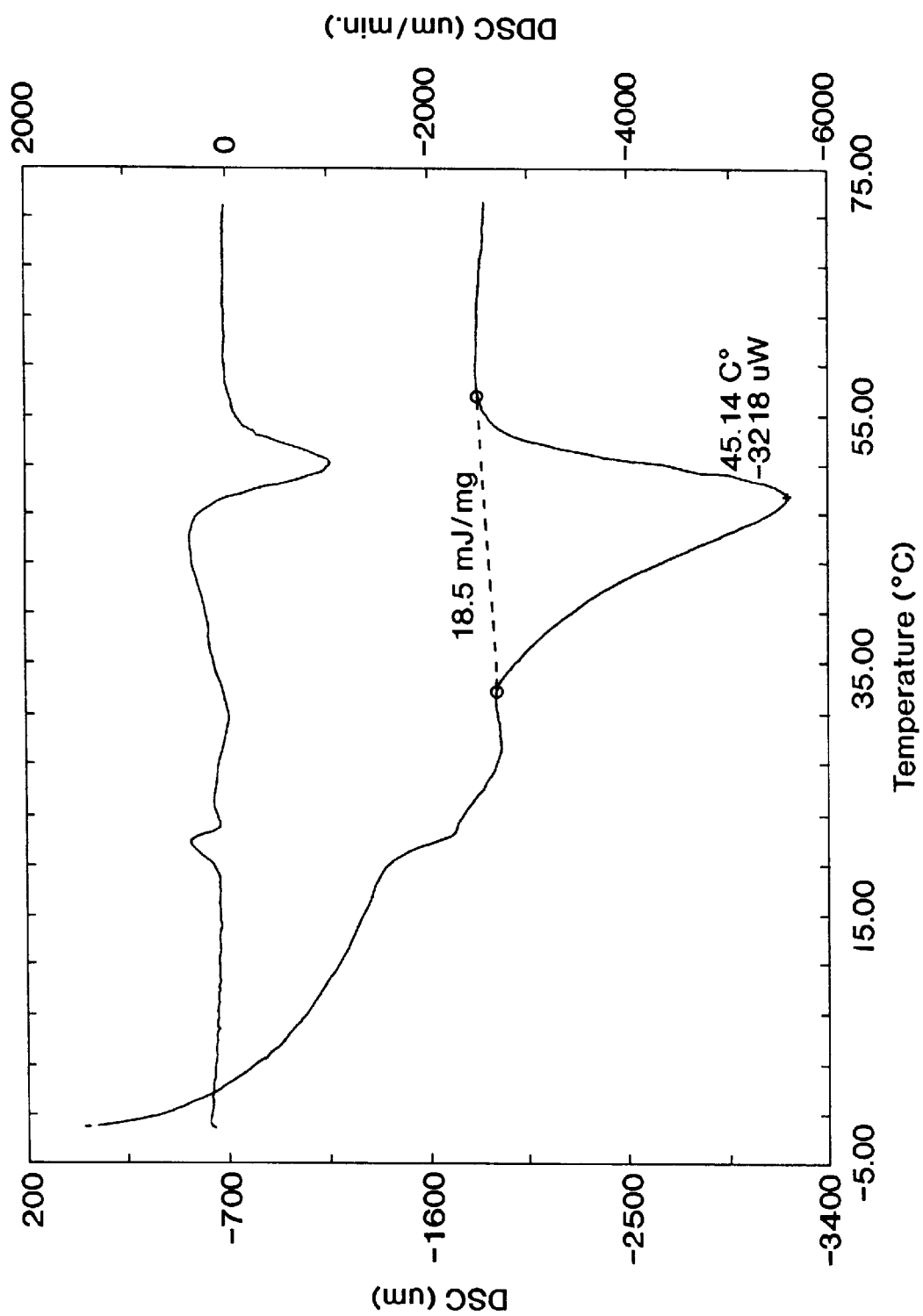
FIG. 5 is a measurement curve obtained with a differential scanning calorimeter to determine the Krafft point of an aqueous solution of 40% sodium N-methyltaurate laurate.

The Krafft points of 30% and 40% aqueous solutions of sodium N-methyltaurate laurate were measured using a differential scanning calorimeter (DSC). The results are shown in FIG. 4 and FIG. 5, respectively. 30% and 40% aqueous solutions of sodium N-methyltaurate laurate showed heat absorption peaks, i.e. Krafft points, at around 38° C. and 45° C., respectively. On the other hand, the Krafft point of sodium laurate, when the concentration is 10% or more, is known to be approximately 20° C. Therefore, it is shown that the Krafft point of sodium N-methyltaurate laurate is higher than this and changes with the concentration. In general, a surfactant is insoluble in water at a temperature lower than its Krafft point. This means less irritation and higher safety. A suggested mechanism is as follows: during washing, sodium N-methyltaurate laurate has a lower Krafft point due to a lower concentration in water and therefore shows a performance close to that of sodium laurate; after washing, as the moisture on the skin evaporates, the Krafft point increases and irritation is reduced compared with conventional sodium laurate soap.

Examples of the detergent composition of the present invention which contain an alkali metal N-methyltaurate salt or organic alkali N-methyltaurate salt of various fatty acids are described below. The blended alkali metal N-methyltaurate salt or organic alkali N-methyltaurate salt of various fatty acids were prepared according to the aforementioned Preparation examples 1 and 2. The blend ratios are expressed in weight percent units.

Example 1
Shampoo

|     | wt % |
| --- | --- |
| (1) Ethylene glycol fatty acid ester | 2.0 |
| (2) Triethanolamine N-methyltaurate laurate | 10.0 |
| (3) Dodecyl maltoside | 5.0 |
| (4) Laurylsulfobetaine | 10.0 |
| (5) Diethanolamide laurate | 5.0 |
| (6) Propylene glycol | 2.0 |
| (7) Coloring agent, perfume | Appropriate amount |
| (8) Purified water | Balance |

(Preparation Method)

Preparation was carried out according to the conventional method.

The shampoo of the present invention exhibited a lower irritation to hair and scalp, superior foaming properties, no stickiness and superior feeling during use.

Example 2
Shampoo

|     | wt % |
| --- | --- |
| (1) Sodium cocoylmethyl taurate | 8.0 |
| (2) Triethanolamine N-methyltaurate salt of coconut fatty acid | 20.0 |
| (3) Sodium N-methyltaurate salt of myristic acid | 2.0 |
| (4) Diethanol amide of coconut fatty acid | 4.0 |
| (5) Perfume | Appropriate amount |
| (6) EDTA.2Na | Appropriate amount |
| (7) Purified water | Balance |

(Preparation Method)

Preparation was carried out according to the conventional method.

The shampoo of the present invention exhibited a lower irritation to hair and scalp, superior foaming properties, no stickiness and superior feeling during use.

Example 3
Body Shampoo

|     | wt % |
| --- | --- |
| (1) Glycerine | 5.0 |
| (2) Potassium N-methyltaurate salt of myristic acid | 5.0 |
| (3) Myristic ester of sucrose | 1.0 |
| (4) Triethanolamine laurate | 10.0 |
| (5) Sodium laurylsulfonsuccinate | 5.0 |
| (6) Diethanol amide of coconut oil | 3.0 |
| (7) Chelating agent | 0.1 |
| (8) Coloring agent, perfume | Appropriate amount |
| (9) Purified water | Balance |

(Preparation Method)

Preparation was carried out according to the conventional method.

The body shampoo of the present invention exhibited a lower irritation to skin, excellent foaming during use, and a moist feeling after washing was completed.

Example 4
Body Shampoo

|     | wt % |
| --- | --- |
| (1) Sorbitol | 2.0 |
| (2) Erythritol | 5.0 |
| (3) Octyl glucoside | 15.0 |
| (4) Sodium N-methyltaurate salt of palmitic acid | 5.0 |
| (5) Diethanol amide of coconut oil | 3.0 |
| (6) Chelating agent | 0.1 |
| (7) Cationized cellulose | 0.2 |
| (8) Coloring agent, perfume | Appropriate amount |
| (9) Purified water | Balance |

(Preparation Method)

Preparation was carried out according to the conventional method.

The body shampoo of the present invention exhibited a lower irritation to skin, excellent foaming during use, and a moist feeling after washing was completed.

Example 5
Liquid Detergent for Clothes

|     | wt % |
| --- | --- |
| (1) Sodium POE (3 moles) lauryl ether sulfate | 10.0 |
| (2) Maltotritol dodecyl ether | 30.0 |
| (3) Lysine N-methyltaurate salt of coconut fatty acid | 15.0 |
| (4) Distearyldimethylammonium chloride | 2.0 |
| (5) Aprotinin | 0.5 |
| (6) Bleach | Appropriate amount |
| (7) Purified water | Balance |

(Preparation Method)

Preparation was carried out according to the conventional method.

The detergent for clothes of the present invention was highly safe and had a superior cleaning capability.

Example 6
Powder Detergent for Clothes

|     | wt % |
| --- | --- |
| (1) LAS-Na | 15.0 |
| (2) Sodium N-methyltaurate salt of coconut fatty acid | 1.0 |
| (3) Octyl glucoside | 3.0 |
| (4) $Na_2SO_4$ | 30.0 |
| (5) 2-phenylacetamide | 2.0 |
| (6) CMC (66%) | 1.5 |
| (7) Metasilicic soda (anhydride) | 20.0 |
| (8) Fluorescent whitening agent | 0.2 |
| (9) $Na_2CO_3$ | Balance |

(Preparation Method)

Preparation was carried out according to the conventional method.

The powder detergent for clothes of the present invention was highly safe and had a superior cleaning capability.

Example 7

Solid Soap

|  | wt % |
|---|---|
| (1) Beef tallow | 20.0 |
| (2) Coconut oil | 12.0 |
| (3) Castor oil | 5.0 |
| (4) Olive oil | 3.0 |
| (5) Sodium hydroxide | 6.0 |
| (6) Ethanol | 20.0 |
| (7) Maltitolhexadecyl ether | 4.0 |
| (8) Sodium N-methyltaurate salt of 2-ethylhexalic acid | 1.0 |
| (9) Glycerine | 5.0 |
| (10) Sucrose | 10.0 |
| (11) Cyclohexylguanidine | 3.0 |
| (12) EDTA | 0.1 |
| (13) Perfume | Appropriate amount |
| (14) Pigment | Appropriate amount |
| (15) Purified water | Balance |

(Preparation Method)

Preparation was carried out according to the conventional method.

The solid soap of the present invention exhibited a lower irritation to skin, excellent foaming during use, and a refreshing feeling after washing was completed.

Example 8

Liquid Soap

|  | wt % |
|---|---|
| (1) Lauric acid | 3.0 |
| (2) Myristic acid | 7.0 |
| (3) Palmitic acid | 3.0 |
| (4) Oleic acid | 2.5 |
| (5) Lauroyldiethanolamide | 6.0 |
| (6) Propylene glycol | 11.0 |
| (7) Erythritol | 4.0 |
| (8) Sodium N-methyltaurate salt of coconut fatty acid | 10.0 |
| (9) Triethanolamine N-methyltaurate salt of lauric acid | 3.0 |
| (10) Sucrose | 5.0 |
| (11) Sodium hydroxide | 3.0 |
| (12) EDTA | 0.1 |
| (13) p-aminobenzamidine | 1.0 |
| (14) Perfume | Appropriate amount |
| (15) Purified water | Balance |

(Preparation Method)

Preparation was carried out according to the conventional method.

The liquid soap of the present invention exhibited a lower irritation to skin, excellent foaming during use, and a refreshing feeling after washing was completed.

Example 9

Kitchen Detergent

|  | wt % |
|---|---|
| (1) Sodium α-oleinsulfonate | 20.0 |
| (2) POE (15 moles) alkyl ether | 8.0 |
| (3) Laurylamidepropyl betaine | 5.0 |
| (4) Ethanol | 1.5 |
| (5) Pigment | Appropriate amount |
| (6) Perfume | Appropriate amount |
| (7) Sodium N-methyltaurate salt of coconut fatty acid | 10.0 |
| (8) Sodium glycerylsulfate laurate | 3.0 |
| (9) Purified water | Balance |

(Preparation Method)

Preparation was carried out according to the conventional method.

The kitchen detergent of the present invention exhibited a lower irritation to skin and excellent cleaning capability.

2. Examples of Claims 5–8

Preparation Example 1

Preparation of Sodium Taurate Laurate 200 g of lauric acid was stirred and dissolved at 80° C. 250 ml of 50% aqueous solution of taurine, 80 ml of 50% aqueous solution of sodium hydroxide and 200 ml of ion exchanged water were added to it and the mixture was stirred. After cooling, the product was taken out from the container and used as the 50% sodium taurate laurate soap.

Preparation Example 2

Preparation of Triethanolamine Taurate Laurate 200 g of lauric acid was stirred and dissolved at 80° C. 250 ml of 50% aqueous solution of taurine, 250 ml of 50% aqueous solution of triethanolamine and 200 ml of ion exchanged water were added to it and the mixture was stirred. After cooling, the product was taken out from the container and used as the original 50% triethanolamine taurate laurate soap.

The alkali metal taurate salt and the organic alkali taurate salt of lauric acid thus prepared were used as test samples for the following tests to prove their efficacy.

[Foaming Test with the Shaking Method]

0.5 wt % of each sample in Table 6 was dissolved in ion exchanged water with 70 ppm calcium chloride already dissolved in it. The pH was then adjusted to 7.0. This solution was kept at 30° C., put into a Nessler's tube with an inner diameter of 3 cm and a height of 20 cm equipped with a sliding plug, and then tilted 90 degrees every second using a pendulum type shaker. After one minute, the sample was taken out of the shaker and the foam height, the foam film thickness and the foam density were measured. The time required for the foam height to be reduced to a half of the original height was also measured. The foam film thickness was measured by taking a photograph of the foam using a microscope at 100 times magnification and calculating the average value on the photograph. The foam density was obtained by sampling 10 ml of the foam and measuring its weight. The measurement results are shown in Table 7.

TABLE 6

| Sample name | Sample No. |
|---|---|
| Sodium taurate laurate | Test sample 1 |
| Triethanolamine taurate laurate | Test sample 2 |
| Sodium laurate | Control sample 1 |
| Potassium laurate | Control sample 2 |
| Magnesium laurate | Control sample 3 |
| Triethanolamine laurate | Control sample 4 |
| Lysine laurate | Control sample 5 |

TABLE 7

| Sample No. | Foam height (cm) | Foam film thickness ($\mu$) | Foam density (g/ml) | Duration (min.) |
|---|---|---|---|---|
| Test sample 1 | 10.6 | 110 | 0.233 | 680 |
| Test sample 2 | 9.6 | 100 | 0.223 | 870 |
| Control sample 1 | 6.5 | 100 | 0.210 | 80 |
| Control sample 2 | 5.5 | 95 | 0.200 | 70 |
| Control sample 3 | 4.7 | 60 | 0.123 | 100 |
| Control sample 4 | 9.0 | 95 | 0.207 | 530 |

In the aforementioned foaming test with the shaking method, the foam height relates to how good the foaming is, the foam film thickness and the foam density relate to the creaminess of the foam, and the duration relates to the durability of the foam at the time of use. A larger value indicates a better performance. As shown in the table, sodium laurate, potassium laurate and magnesium laurate are harder to foam at pH 7 because they are salts of a weak acid and a strong base. On the other hand, the alkali metal taurate salt of a fatty acid and the organic alkali taurate salt of a fatty acid, which are the surfactants used in the present invention, as well as triethanolamine or a lysine salt of a fatty acid foam well at a more acidic pH because they are salts of a weak acid or a weak base. However, triethanolamine laurate and lysine laurate have lower Krafft points and are liquid at room temperature. Therefore they cannot be used for detergents with a solid formulation. Also, the detergent compositions of the present invention are also shown to be superior in terms of the creaminess and durability of the foam. These results indicate that the test samples, the alkali metal taurate salt of a fatty acid and the organic alkali taurate salt of a fatty acid, are compounds which have superior effects as surfactants.

[Sensory Test of the Odor]

A sensory test of the odor was conducted for the aforementioned test samples and control samples. The results are shown in Table 8.

TABLE 8

| Sample No. | Odor |
|---|---|
| Test sample | No odor |
| Test sample | No odor |
| Control sample | No odor |
| Control sample | No odor |
| Control sample | No odor |
| Control sample | Ammonia-like odor |
| Control sample | Ammonia-like odor |

As shown above, the alkali metal taurate salt of a fatty acid and the organic alkali taurate salt of a fatty acid, which are the surfactants used in the present invention, are salts of a fatty acid and a weak base and yet, similar to alkali metal salts or alkali earth metal salts of a fatty acid, they don't have an offensive odor. This is believed to be due to the fact that they, unlike triethanolamine or lysine, have sulfonate, which is a strong acid, in the same molecule and therefore do not evaporate easily.

[Sensory Test of Actual Use]

Fifty panelists were used to conduct the actual use test for Test samples 1 and 2 as well as Control samples 1–5 shown in Table 6. The test was conducted as follows. 5 ml of a 10% aqueous solution of each sample was put on a hand and the hand was washed for 30 seconds. The feeling during use and after rinsing was rated with a five point scale based on the criteria shown in Table 9. The average of the fifty panelists was calculated to obtain the total evalution. The results are shown in Table 10.

TABLE 9

| | Evaluation Point | | | | |
|---|---|---|---|---|---|
| Item | 5 | 4 | 3 | 2 | 1 |
| Foaming | Very good | Somewhat good | Normal | Somewhat poor | Very poor |
| Creaminess of the foam | Very good | Somewhat good | Normal | Somewhat poor | Very poor |
| Refreshing feeling after use | Very refreshing | Somewhat refreshing | Normal | Somewhat slimy | Very slimy |
| Moist feeling after drying | Very moist | Somewhat moist | Normal | Somewhat stretched | Very stretched |

⊚: The average of the evaluation points is 4–5.
o: The average of the evaluation points is 3–3.9.
Δ: The average of the evaluation points is 2–2.9.
x: The average of the evaluation points is 1–1.9.

TABLE 10

| Sample No. | Foaming | Creaminess of the foam | Refreshing feeling after use | Moist feeling after drying |
|---|---|---|---|---|
| Test sample 1 | ⊚ | ⊚ | ⊚ | ⊚ |
| Test sample 2 | ⊚ | ⊚ | o | ⊚ |
| Control sample 1 | ⊚ | o | ⊚ | x |
| Control sample 2 | o | Δ | o | x |
| Control sample 3 | ⊚ | o | Δ | Δ |
| Control sample 4 | o | o | x | ⊚ |
| Control sample 5 | o | ⊚ | Δ | o |

Comparison between samples in Table 10 with the same alkali portion indicates that insertion of taurine in the structure improves all the feelings during use. The reason why an amphoteric compound which has both strong acid and weak base (–NH$_2$) functional groups, such as taurine, has the aforementioned effects is believed to be as follows: during washing when there is plenty of water, the —COO$^-$ group of the fatty acid dissociates to give a feeling close to sodium soap, whereas after use when it is dry and there is not much water, the —COO$^-$ group of the fatty acid forms an ion pair with the N$^+$ portion of taurine and the melting point of the hydrated crystal, dependent on the concentration, rises to cause insolubility in water and produce the feeling of use of sulfonic acid type surfactants. This is believed to be the reason why the feeling of use of the detergent composition of the present invention is moist after drying.

Examples of the detergent composition of the present invention which contain an alkali metal taurate salt or organic alkali taurate salt of various fatty acids are described below. The blended alkali metal taurate salt or organic alkali taurate salt of various fatty acids were prepared according to the aforementioned Preparation examples 1 and 2. The blend ratios are expressed in weight percent units.

Example 1

Shampoo

|     |                                  | wt %               |
| --- | -------------------------------- | ------------------ |
| (1) | Ethylene glycol fatty acid ester | 2.0                |
| (2) | Triethanolamine taurate laurate  | 10.0               |
| (3) | Dodecyl maltoside                | 5.0                |
| (4) | Laurylsulfobetaine               | 10.0               |
| (5) | Diethanolamide laurate           | 5.0                |
| (6) | Propylene glycol                 | 2.0                |
| (7) | Coloring agent, perfume          | Appropriate amount |
| (8) | Purified water                   | Balance            |

(Preparation Method)

Preparation was carried out according to the conventional method.

The shampoo of the present invention exhibited a lower irritation to hair and scalp, superior foaming properties, no stickiness and superior feeling during use.

Example 2

Shampoo

|     |                                               | wt %               |
| --- | --------------------------------------------- | ------------------ |
| (1) | Sodium cocoylmethyl taurate                   | 8.0                |
| (2) | Triethanolamine taurate salt of coconut fatty acid | 20.0          |
| (3) | Sodium taurate salt of myristic acid          | 2.0                |
| (4) | Diethanol amide of coconut fatty acid         | 4.0                |
| (5) | Perfume                                       | Appropriate amount |
| (6) | EDTA · 2Na                                    | Appropriate amount |
| (7) | Purified water                                | Balance            |

(Preparation Method)

Preparation was carried out according to the conventional method.

The shampoo of the present invention exhibited a lower irritation to hair and scalp, superior foaming properties, no stickiness and superior feeling during use.

Example 3

Body Shampoo

|     |                                        | wt %               |
| --- | -------------------------------------- | ------------------ |
| (1) | Glycerine                              | 5.0                |
| (2) | Potassium taurate salt of myristic acid | 5.0               |
| (3) | Myristic ester of sucrose              | 1.0                |
| (4) | Triethanolamine laurate                | 10.0               |
| (5) | Sodium laurylsulfonsuccinate           | 5.0                |
| (6) | Diethanol amide of coconut oil         | 3.0                |
| (7) | Chelating agent                        | 0.1                |
| (8) | Coloring agent, perfume                | Appropriate amount |
| (9) | Purified water                         | Balance            |

(Preparation Method)

Preparation was carried out according to the conventional method.

The body shampoo of the present invention exhibited a lower irritation to skin, excellent foaming during use, and a moist feeling after washing was achieved.

Example 4

Body Shampoo

|     |                                       | wt %               |
| --- | ------------------------------------- | ------------------ |
| (1) | Sorbitol                              | 2.0                |
| (2) | Erythritol                            | 5.0                |
| (3) | Octyl glucoside                       | 15.0               |
| (4) | Sodium taurate salt of palmitic acid  | 5.0                |
| (5) | Diethanol amide of coconut acid       | 3.0                |
| (6) | Chelating agent                       | 0.1                |
| (7) | Cationized cellulose                  | 0.2                |
| (8) | Coloring agent, perfume               | Appropriate amount |
| (9) | Purified water                        | Balance            |

(Preparation Method)

Preparation was carried out according to the conventional method.

The body shampoo of the present invention exhibited a lower irritation to skin, excellent foaming during use, and a moist feeling after washing was completed.

Example 5

Liquid Detergent for Clothes

|     |                                          | wt %               |
| --- | ---------------------------------------- | ------------------ |
| (1) | Sodium POE (3 moles) lauryl ether sulfate | 10.0              |
| (2) | Maltotritol dodecyl ether                | 30.0               |
| (3) | Lysine taurate salt of coconut fatty acid | 15.0              |
| (4) | Distearyldimethylammonium chloride       | 2.0                |
| (5) | Aprotinin                                | 0.5                |
| (6) | Bleach                                   | Appropriate amount |
| (7) | Purified water                           | Balance            |

(Preparation Method)

Preparation was carried out according to the conventional method.

The detergent for clothes of the present invention was highly safe and had a superior cleaning capability.

Example 6
Powder Detergent for Clothes

|     |                                         | wt %    |
| --- | --------------------------------------- | ------- |
| (1) | LAS-Na                                  | 15.0    |
| (2) | Sodium taurate salt of coconut fatty acid | 1.0   |
| (3) | Octyl glucoside                         | 3.0     |
| (4) | $Na_2SO_4$                              | 30.0    |
| (5) | 2-phenylacetamide                       | 2.0     |
| (6) | CMC (66%)                               | 1.5     |
| (7) | Metasilicic soda (anhydride)            | 20.0    |
| (8) | Fluroescent whitening agent             | 0.2     |
| (9) | $Na_2CO_3$                              | Balance |

(Preparation Method)

Preparation was carried out according to the conventional method.

The powder detergent for clothes of the present invention was highly safe and had a superior cleaning capability.

Example 7
Solid Soap

|      |                                          | wt %               |
| ---- | ---------------------------------------- | ------------------ |
| (1)  | Beef tallow                              | 20.0               |
| (2)  | Coconut oil                              | 12.0               |
| (3)  | Castor oil                               | 5.0                |
| (4)  | Olive oil                                | 3.0                |
| (5)  | Sodium hydroxide                         | 6.0                |
| (6)  | Ethanol                                  | 20.0               |
| (7)  | Maltitolhexadecyl ether                  | 4.0                |
| (8)  | Sodium taurate salt of 2-ethylhexalic acid | 1.0              |
| (9)  | Glycerine                                | 5.0                |
| (10) | Sucrose                                  | 10.0               |
| (11) | Cyclohexylguanidine                      | 3.0                |
| (12) | EDTA                                     | 0.1                |
| (13) | Perfume                                  | Appropriate amount |
| (14) | Pigment                                  | Appropriate amount |
| (15) | Purified water                           | Balance            |

(Preparation Method)

Preparation was carried out according to the conventional method.

The solid soap of the present invention exhibited a lower irritation to skin, excellent foaming during use, and a refreshing feeling after washing was completed.

Example 8
Liquid Soap

|      |                                          | wt % |
| ---- | ---------------------------------------- | ---- |
| (1)  | Lauric acid                              | 3.0  |
| (2)  | Myristic acid                            | 7.0  |
| (3)  | Palmitic acid                            | 3.0  |
| (4)  | Oleic acid                               | 2.5  |
| (5)  | Lauroyldiethanolamide                    | 6.0  |
| (6)  | Propylene glycol                         | 11.0 |
| (7)  | Erythritol                               | 4.0  |
| (8)  | Sodium taurate salt of coconut fatty acid | 10.0 |
| (9)  | Triethanolamine taurate salt of lauric acid | 3.0 |
| (10) | Sucrose                                  | 5.0  |
| (11) | Sodium hydroxide                         | 3.0  |
| (12) | EDTA                                     | 0.1  |

-continued

|      |                  | wt %               |
| ---- | ---------------- | ------------------ |
| (13) | p-aminobenzamidine | 1.0              |
| (14) | Perfume          | Appropriate amount |
| (15) | Purified water   | Balance            |

(Preparation Method)

Preparation was carried out according to the conventional method.

The liquid soap of the present invention exhibited a lower irritation to skin, excellent foaming during use, and a refreshing feeling after washing was completed.

Example 9
Kitchen Detergent

|     |                                          | wt %               |
| --- | ---------------------------------------- | ------------------ |
| (1) | Sodium α-oleinsulfonate                  | 20.0               |
| (2) | POE (15 moles) alkyl ether               | 8.0                |
| (3) | Laurylamidepropyl betaine                | 5.0                |
| (4) | Ethanol                                  | 1.5                |
| (5) | Pigment                                  | Appropriate amount |
| (6) | Perfume                                  | Appropriate amount |
| (7) | Sodium taurate salt of coconut fatty acid | 10.0              |
| (8) | Sodium glycerylsulfate laurate           | 3.0                |
| (9) | Purified water                           | Balance            |

(Preparation Method)

Preparation was carried out according to the conventional method.

The kitchen detergent of the present invention exhibited a lower irritation to skin and excellent cleaning capability.

3. Examples of Claims 9–12

Preparation Example 1
Preparation of Sodium Hypotaurate Laurate 200 g of lauric acid was stirred and dissolved at 80° C. 218 ml of 50% aqueous solution of hypotaurine, 80 ml of 50% aqueous solution of sodium hydroxide and 200 ml of ion exchanged water were added to it and the mixture was stirred. After cooling, the product was taken out from the container and used as the 50% sodium hypotaurate laurate soap.

Preparation Example 2
Preparation of Triethanolamine Hypotaurate Laurate 200 g of lauric acid was stirred and dissolved at 80° C. 218 ml of 50% aqueous solution of hypotaurine, 250 ml of 50% aqueous solution of triethanolamine and 200 ml of ion exchanged water were added to it and the mixture was stirred. After cooling, the product was taken out from the container and used as the original 50% triethanolamine hypotaurate laurate soap.

The alkali metal hypotaurate salt and the organic alkali hypotaurate salt of lauric acid thus prepared were used as test samples for the following tests to prove their efficacy.

[Foaming Test with the Shaking Method]

0.5 wt % of each sample in Table 11 was dissolved in ion exchanged water with 70 ppm calcium chloride already dissolved in it. The pH was then adjusted to 7.0. This solution was kept at 30° C., put into a Nessler's tube with an inner diameter of 3 cm and a height of 20 cm equipped with a sliding plug, and then tilted 90 degrees every second using a pendulum type shaker. After one minute, the sample was taken out of the shaker and the foam height, the foam film thickness and the foam density were measured. The time required for the foam height to be reduced to a half of the original height was also measured. The foam film thickness was measured by taking a photograph of the foam using a microscope at 100 times magnification and calculating the average value on the photograph. The foam density was obtained by sampling 10 ml of the foam and measuring its weight. The measurement results are shown in Table 12.

TABLE 11

| Sample name | Sample No. |
| --- | --- |
| Sodium hypotaurate laurate | Test sample 1 |
| Triethanolamine hypotaurate laurate | Test sample 2 |
| Sodium laurate | Control sample 1 |
| Potassium laurate | Control sample 2 |
| Magnesium laurate | Control sample 3 |
| Triethanolamine laurate | Control sample 4 |
| Lysine laurate | Control sample 5 |

TABLE 12

| Sample No. | Foam height (cm) | Foam film thickness ($\mu$) | Foam density (g/ml) | Duration (min.) |
| --- | --- | --- | --- | --- |
| Test sample 1 | 10.3 | 105 | 0.241 | 570 |
| Test sample 2 | 9.4 | 100 | 0.248 | 850 |
| Control sample 1 | 6.5 | 100 | 0.210 | 80 |
| Control sample 2 | 5.5 | 95 | 0.200 | 70 |
| Control sample 3 | 4.7 | 60 | 0.123 | 100 |
| Control sample 4 | 9.0 | 95 | 0.207 | 530 |
| Control sample 5 | 9.3 | 100 | 0.240 | 540 |

In the aforementioned foaming test with the shaking method, the foam height relates to how good the foaming is, the foam film thickness and the foam density relate to the creaminess of the foam, and the duration relates to the durability of the foam at the time of use. A larger value indicates a better performance. As shown in the table, sodium laurate, potassium laurate and magnesium laurate are harder to foam at pH 7 because they are salts of a weak acid and a strong base. On the other hand, the alkali metal hypotaurate salt of a fatty acid and the organic alkali hypotaurate salt of a fatty acid, which are the surfactants used in the present invention, as well as triethanolamine or a lysine salt of a fatty acid foam well at a more acidic pH because they are salts of a weak acid or a weak base. However, triethanolamine laurate and lysine laurate have lower Krafft points and are liquid at room temperature. Therefore they cannot be used for detergents with a solid formulation. Also, the detergent compositions of the present invention are also shown to be superior in terms of the creaminess and durability of the foam. These results indicate that the test samples, the alkali metal hypotaurate salt of a fatty acid and the organic alkali hypotaurate salt of a fatty acid, are compounds which have superior effects as surfactants.

[Sensory Test of the Odor]

A sensory test of the odor was conducted for the aforementioned test samples and control samples. The results are shown in Table 13.

TABLE 13

| Sample No. | Odor |
| --- | --- |
| Test sample 1 | No odor |
| Test sample 2 | No odor |
| Control sample 1 | No odor |
| Control sample 2 | No odor |
| Control sample 3 | No odor |
| Control sample 4 | Ammonia-like odor |
| Control sample 5 | Ammonia-like odor |

As shown above, the alkali metal hypotaurate salt of a fatty acid and the organic alkali hypotaurate salt of a fatty acid, which are the surfactants used in the present invention, are salts of a fatty acid and a weak base and yet, similar to alkali metal salts or alkali earth metal salts of a fatty acid, they don't have an offensive odor. This is believed to be due to the fact that they, unlike triethanolamine or lysine, have sulfonate, which is a strong acid, in the same molecule and therefore do not evaporate easily.

[Sensory Test of Actual Use]

Fifty panelists were used to conduct the actual use test for Test samples 1 and 2 as well as Control samples 1–5 shown in Table 11. The test was conducted as follows. 5 ml of a 10% aqueous solution of each sample was put on a hand and the hand was washed for 30 seconds. The feeling during use and after rinsing was rated with a five point scale based on the criteria shown in Table 14. The average of the fifty panelists was calculated to obtain the total evaluation. The results are shown in Table 15.

TABLE 14

| Item | Evaluation Point | | | | |
| --- | --- | --- | --- | --- | --- |
|  | 5 | 4 | 3 | 2 | 1 |
| Foaming | Very good | Somewhat good | Normal | Somewhat poor | Very poor |
| Creaminess of the foam | Very good | Somewhat good | Normal | Somewhat poor | Very poor |
| Refreshing feeling after use | Very refreshing | Somewhat refreshing | Normal | Somewhat slimy | Very slimy |
| Moist feeling after drying | Very moist | Somewhat moist | Normal | Somewhat stretched | Very stretched |

TABLE 15

| Sample No. | Foaming | Creaminess of the foam | Refreshing feeling after use | Moist feeling after drying |
| --- | --- | --- | --- | --- |
| Test sample 1 | ⊚ | ⊚ | ⊚ | ⊚ |
| Test sample 2 | ⊚ | ⊚ | ○ | ⊚ |
| Control sample 1 | ⊚ | ○ | ⊚ | X |
| Control sample 2 | ○ | Δ | ○ | X |
| Control sample 3 | ⊚ | ○ | Δ | Δ |
| Control sample 4 | ○ | ○ | X | ⊚ |

⊚: The average of the evaluation points is 4–5.
○: The average of the evaluation points is 3–3.9.
Δ: The average of the evaluation points is 2–2.9.
X: The average of the evaluation points is 1–1.9.

Comparison between samples in Table 15 with the same alkali portion indicates that insertion of hypotaurine in the structure improves all the feelings during use. The reason why an amphoteric compound which has both strong acid and weak base (—NH$_2$) functional groups, such as hypotaurine, has the aforementioned effects is believed to be as follows: during washing when there is plenty of water, the —COO$^-$ group of the fatty acid dissociates to give a feeling close to sodium soap, whereas after use when it is dry and there is not much water, the —COO$^{31}$ group of the fatty acid forms an ion pair with the N$^+$ portion of hypotaurine and the melting point of the hydrated crystal, dependent on the concentration, rises to cause insolubility in water and produce the feeling of use of sulfonic acid type surfactants. This is believed to be the reason why the feeling of use of the detergent composition of the present invention is moist after drying.

Examples of the detergent composition of the present invention which contain an alkali metal hypotaurate salt or organic alkali hypotaurate salt of various fatty acids are described below. The blended alkali metal hypotaurate salt or organic alkali hypotaurate salt of various fatty acids were prepared according to the aforementioned Preparation examples 1 and 2. The blend ratios are expressed in weight percent units.

Example 1
Shampoo

|  | wt % |
|---|---|
| (1) Ethylene glycol fatty acid ester | 2.0 |
| (2) Triethanolamine hypotaurate laurate | 10.0 |
| (3) Dodecyl maltoside | 5.0 |
| (4) Laurylsulfobetaine | 10.0 |
| (5) Diethanolamide laurate | 5.0 |
| (6) Propylene glycol | 2.0 |
| (7) Coloring agent, perfume | Appropriate amount |
| (8) Purified water | Balance |

(Preparation Method)

Preparation was carried out according to the conventional method.

The shampoo of the present invention exhibited a lower irritation to hair and scalp, superior foaming properties, no stickiness and superior feeling during use.

Example 2
Shampoo

|  | wt % |
|---|---|
| (1) Sodium cocoylmethyl hypotaurate | 8.0 |
| (2) Triethanolamine hypotaurate salt of coconut fatty acid | 20.0 |
| (3) Sodium hypotaurate salt of myristic acid | 2.0 |
| (4) Diethanol amide of coconut fatty acid | 4.0 |
| (5) Perfume | Appropriate amount |
| (6) EDTA.2Na | Appropriate amount |
| (7) Purified water | Balance |

(Preparation Method)

Preparation was carried out according to the conventional method.

The shampoo of the present invention exhibited a lower irritation to hair and scalp, superior foaming properties, no stickiness and superior feeling during use.

Example 3
Body Shampoo

|  | wt % |
|---|---|
| (1) Glycerine | 5.0 |
| (2) Potassium hypotaurate salt of myristic acid | 5.0 |
| (3) Myristic ester of sucrose | 1.0 |
| (4) Triethanolamine laurate | 10.0 |
| (5) Sodium laurylsulfonsuccinate | 5.0 |
| (6) Diethanol amide of coconut oil | 3.0 |
| (7) Chelating agent | 0.1 |
| (8) Coloring agent, perfume | Appropriate amount |
| (9) Purified water | Balance |

(Preparation Method)

Preparation was carried out according to the conventional method.

The body shampoo of the present invention exhibited a lower irritation to skin, excellent foaming during use, and a moist feeling after washing was completed.

Example 4
Body Shampoo

|  | wt % |
|---|---|
| (1) Sorbitol | 2.0 |
| (2) Erythritol | 5.0 |
| (3) Octyl glucoside | 15.0 |
| (4) Sodium hypotaurate salt of palmitic acid | 5.0 |
| (5) Diethanol amide of coconut oil | 3.0 |
| (6) Chelating agent | 0.1 |
| (7) Cationized cellulose | 0.2 |
| (8) Coloring agent, perfume | Appropriate amount |
| (9) Purified water | Balance |

(Preparation Method)

Preparation was carried out according to the conventional method.

The body shampoo of the present invention exhibited a lower irritation to skin, excellent foaming during use, and a moist feeling after washing was completed.

Example 5
Liquid Detergent for Clothes

|  | wt % |
|---|---|
| (1) Sodium POE (3 moles) lauryl ether sulfate | 10.0 |
| (2) Maltotritol dodecyl ether | 30.0 |
| (3) Lysine hypotaurate salt of coconut fatty acid | 15.0 |
| (4) Distearyldimethylammonium chloride | 2.0 |
| (5) Aprotinin | 0.5 |
| (6) Bleach | Appropriate amount |
| (7) Purified water | Balance |

(Preparation Method)

Preparation was carried out according to the conventional method.

The detergent for clothes of the present invention was highly safe and had a superior cleaning capability.

Example 6
Powder Detergent for Clothes

| | wt % |
|---|---|
| (1) LAS-Na | 15.0 |
| (2) Sodium hypotaurate salt of coconut fatty acid | 1.0 |
| (3) Octyl glucoside | 3.0 |
| (4) Na$_2$SO$_4$ | 30.0 |
| (5) 2-phenylacetamide | 2.0 |
| (6) CMC (66%) | 1.5 |
| (7) Metasilicic soda (anhydride) | 20.0 |
| (8) Fluorescent whitening agent | 0.2 |
| (9) Na$_2$CO$_3$ | Balance |

(Preparation Method)
Preparation was carried out according to the conventional method.
The powder detergent for clothes of the present invention was highly safe and had a superior cleaning capability.

Example 7
Solid Soap

| | wt % |
|---|---|
| (1) Beef tallow | 20.0 |
| (2) Coconut oil | 12.0 |
| (3) Castor oil | 5.0 |
| (4) Olive oil | 3.0 |
| (5) Sodium hydroxide | 6.0 |
| (6) Ethanol | 20.0 |
| (7) Maltitolhexadecyl ether | 4.0 |
| (8) Sodium hypotaurate salt of 2-ethylhexalic acid | 1.0 |
| (9) Glycerine | 5.0 |
| (10) Sucrose | 10.0 |
| (11) Cyclohexylguanidine | 3.0 |
| (12) EDTA | 0.1 |
| (13) Perfume | Appropriate amount |
| (14) Pigment | Appropriate amount |
| (15) Purified water | Balance |

(Preparation Method)
Preparation was carried out according to the conventional method.
The solid soap of the present invention exhibited a lower irritation to skin, excellent foaming during use, and a refreshing feeling after washing was completed.

Example 8
Liquid Soap

| | wt % |
|---|---|
| (1) Lauric acid | 3.0 |
| (2) Myristic acid | 7.0 |
| (3) Palmitic acid | 3.0 |
| (4) Oleic acid | 2.5 |
| (5) Lauroyldiethanolamide | 6.0 |
| (6) Propylene glycol | 11.0 |
| (7) Erythritol | 4.0 |
| (8) Sodium hypotaurate salt of coconut fatty acid | 10.0 |
| (9) Triethanolamine hypotaurate salt of lauric acid | 3.0 |
| (10) Sucrose | 5.0 |
| (11) Sodium hydroxide | 3.0 |
| (12) EDTA | 0.1 |
| (13) p-aminobenzamidine | 1.0 |
| (14) Perfume | Appropriate amount |
| (15) Purified water | Balance |

(Preparation Method)
Preparation was carried out according to the conventional method.
The liquid soap of the present invention exhibited a lower irritation to skin, excellent foaming during use, and a refreshing feeling after washing was completed.

Example 9
Kitchen Detergent

| | wt % |
|---|---|
| (1) Sodium α-oleinsulfonate | 20.0 |
| (2) POE (15 moles) alkyl ether | 8.0 |
| (3) Laurylamidepropyl betaine | 5.0 |
| (4) Ethanol | 1.5 |
| (5) Pigment | Appropriate amount |
| (6) Perfume | Appropriate amount |
| (7) Sodium hypotaurate salt of coconut fatty acid | 10.0 |
| (8) Sodium glycerylsulfate laurate | 3.0 |
| (9) Purified water | Balance |

(Preparation Method)
Preparation was carried out according to the conventional method.
The kitchen detergent of the present invention exhibited a lower irritation to skin and excellent cleaning capability.

4. Examples of Claims 13–20
[The Foaming Test with the Shaking Method] and [The Sensory Test of the Odor]

0.5 wt % of each sample was dissolved in ion exchanged water with 70 ppm calcium chloride already dissolved in it. The pH was then adjusted to 7.0. This solution was kept at 30° C., put into a Nessler's tube with an inner diameter of 3 cm and a height of 20 cm equipped with a sliding plug, and then tilted 90 degrees every second using a pendulum type shaker. After one minute, the sample was taken out of the shaker and the foam height, the foam film thickness and the foam density were measured. The time required for the foam height to be reduced to a half of the original height was also measured. The foam film thickness was measured by taking a photograph of the foam using a microscope at 100 times magnification and calculating the average value on the photograph. The foam density was obtained by sampling 10 ml of the foam and measuring its weight. The test samples and the measurement results are shown in the following tables. In the aforementioned foaming test with the shaking method, the foam height relates to how good the foaming is, the foam film thickness and the foam density relate to the creaminess of the foam, and the duration relates to the durability of the foam at the time of use. A larger value indicates a better performance. A sensory test of the odor was then conducted for the test samples and control samples. The results are shown in tables below.

TABLE 16

| Sample name | Sample No. |
| --- | --- |
| Sodium N-methyltaurate hydroxylaurate | Test sample 1 |
| Triethanolamine taurate hydroxylaurate | Test sample 2 |
| Sodium hydroxylaurate | Control sample 1 |
| Potassium hydroxylaurate | Control sample 2 |
| Triethanolamine hydroxylaurate | Control sample 3 |
| Lysine hydroxylaurate | Control sample 4 |

| Sample No. | Foam height (cm) | Foam film thickness ($\mu$) | Foam density (g/ml) | Duration (min.) |
| --- | --- | --- | --- | --- |
| Test sample 1 | 11.3 | 115 | 0.254 | 890 |
| Test sample 2 | 10.3 | 105 | 0.232 | 1170 |
| Control sample 1 | 7.4 | 107 | 0.213 | 90 |
| Control sample 2 | 6.6 | 100 | 0.210 | 80 |
| Control sample 3 | 10.3 | 100 | 0.219 | 630 |
| Control sample 4 | 10.1 | 100 | 0.239 | 670 |

| Sample No. | Odor |
| --- | --- |
| Test sample 1 | No odor |
| Test sample 2 | No odor |
| Control sample 1 | No odor |
| Control sample 2 | No odor |
| Control sample 3 | Offensive odor |
| Control sample 4 | Offensive odor |

As shown above, sodium hydroxylaurate and potassium hydroxylaurate are harder to foam at pH 7 because they are salts of a weak acid and a strong base. On the other hand, the alkali metal taurate and/or N-methyltaurate salt of a hydroxy-fatty acid and the organic alkali taurate and/or N-methyltaurate salt of a hydroxy-fatty acid, which are the surfactants used in the present invention, as well as triethanolamine or a lysine salt of a hydroxy-fatty acid foam well at a more acidic pH because they are salts of a weak acid or a weak base. However, triethanolamine hydroxy-laurate and lysine hydroxy-laurate have lower Krafft points and are liquid at room temperature. Therefore they cannot be used for detergents with a solid formulation. Also, the detergent compositions of the present invention are also shown to be superior in terms of the creaminess and durability of the foam.

Also, the alkali metal taurate and/or N-methyltaurate salt of a hydroxy-fatty acid and the organic alkali taurate and/or N-methyltaurate salt of a hydroxy-fatty acid, which are the surfactants used in the present invention, are salts of a hydroxy-fatty acid and a weak base and yet, similar to alkali metal salts of a hydroxy-fatty acid, they don't have an offensive odor.

TABLE 17

| Sample name | Sample No. |
| --- | --- |
| Sodium hypotaurate hydroxylaurate | Test sample 1 |
| Triethanolamine hypotaurate hydroxylaurate | Test sample 2 |
| Sodium hydroxylaurate | Control sample 1 |
| Potassium hydroxylaurate | Control sample 2 |
| Triethanolamine hydroxylaurate | Control sample 3 |
| Lysine hydroxylaurate | Control sample 4 |

| Sample No. | Foam height (cm) | Foam film thickness ($\mu$) | Foam density (g/ml) | Duration (min.) |
| --- | --- | --- | --- | --- |
| Test sample 1 | 11.1 | 120 | 0.258 | 910 |
| Test sample 2 | 10.5 | 115 | 0.270 | 1070 |
| Control sample 1 | 7.4 | 107 | 0.213 | 90 |
| Control sample 2 | 6.6 | 100 | 0.210 | 80 |
| Control sample 3 | 10.0 | 100 | 0.219 | 630 |
| Control sample 4 | 10.0 | 100 | 0.239 | 670 |

| Sample No. | Odor |
| --- | --- |
| Test sample 1 | No odor |
| Test sample 2 | No odor |
| Control sample 1 | No odor |
| Control sample 2 | No odor |
| Control sample 3 | Offensive odor |

As shown above, sodium hydroxylaurate and potassium hydroxylaurate are harder to foam at pH 7 because they are salts of a weak acid and a strong base. On the other hand, the alkali metal hypotaurate salt of a hydroxy-fatty acid and the organic alkali hypotaurate salt of a hydroxy-fatty acid, which are the surfactants used in the present invention, as well as triethanolamine or a lysine salt of a hydroxy-fatty acid foam well at a more acidic pH because they are salts of a weak acid or a weak base. However, the detergent compositions of the present invention are shown to be superior in terms of the creaminess and durability of the foam.

Also, the alkali metal hypotaurate salt of a hydroxy-fatty acid and the organic alkali hypotaurate salt of a hydroxy-fatty acid, which are the surfactants used in the present invention, are salts of a hydroxy-fatty acid and a weak base and yet, similar to alkali metal salts and alkali earth metal salts of a hydroxy-fatty acid, they don't have an offensive odor.

TABLE 18

The test solutions for the foaming test with the shaking method was adjusted to pH 4.

| Sample name | Sample No. |
| --- | --- |
| Sodium taurate hydroxylauryl ether carboxylate | Test sample 1 |
| Triethanolamine N-methyltaurate hydroxylauryl ether carboxylate | Test sample 2 |
| Sodium hydroxylauryl ether carboxylate | Control sample 1 |
| Potassium hydroxylauryl ether carboxylate | Control sample 2 |
| Triethanolamine hydroxylauryl ether carboxylate | Control sample 3 |
| Lysine hydroxylauryl ether carboxylate | Control sample 4 |

| Sample No. | Foam height (cm) | Foam film thickness ($\mu$) | Foam density (g/ml) | Duration (min.) |
| --- | --- | --- | --- | --- |
| Test sample 1 | 17.8 | 120 | 0.251 | 1030 |
| Test sample 2 | 16.7 | 115 | 0.254 | 1180 |
| Control sample 1 | 4.1 | 60 | 0.193 | 430 |
| Control sample 2 | 5.9 | 65 | 0.170 | 440 |
| Control sample 3 | 16.3 | 90 | 0.189 | 710 |
| Control sample 4 | 15.1 | 90 | 0.177 | 720 |

| Sample No. | Odor |
| --- | --- |
| Test sample 1 | No odor |
| Test sample 2 | No odor |
| Control sample 1 | No odor |
| Control sample 2 | No odor |

As shown above, sodium hydroxylauryl ether carboxylate and potassium hydroxylauryl ether carboxylate are harder to foam at pH 4. On the other hand, the sodium taurate and/or N-methyltaurate salt of a hydroxylauryl ether carboxylic acid of the present invention and triethanolamine or a lysine salt of a hydroxylauryl ether carboxylic acid foam well at a more acidic pH. However, the detergent compositions of the present invention are also shown to be superior in terms of the creaminess and durability of the foam, compared with the triethanolamine hydroxylauryl ether carboxylate and lysine hydroxylauryl ether carboxylate.

Also, the alkali metal taurate and/or N-methyltaurate salt of a hydroxylauryl ether carboxylic acid and the organic alkali taurate and/or N-methyltaurate salt of a hydroxylauryl ether carboxylic acid of the present invention are salts of a hydroxy-fatty acid and a weak base and yet, similar to alkali metal salts and alkali earth metal salts of a hydroxy-fatty acid, they don't have an offensive odor.

TABLE 19

The test solutions for the foaming test with the shaking method was adjusted to pH 4.

| Sample name | Sample No. |
|---|---|
| Sodium hypotaurate hydroxylauryl ether carboxylate | Test sample 1 |
| Triethanolamine hypotaurate hydroxylauryl ether carboxylate | Test sample 2 |
| Sodium hydroxylauryl ether carboxylate | Control sample 1 |
| Potassium hydroxylauryl ether carboxylate | Control sample 2 |
| Triethanolamine hydroxylauryl ether carboxylate | Control sample 3 |
| Lysine hydroxylauryl ether carboxylate | Control sample 4 |

| Sample No. | Foam height (cm) | Foam film thickness (µ) | Foam density (g/ml) | Duration (min.) |
|---|---|---|---|---|
| Test sample 1 | 17.1 | 115 | 0.233 | 930 |
| Test sample 2 | 16.5 | 115 | 0.242 | 1080 |
| Control sample 1 | 4.1 | 60 | 0.193 | 430 |
| Control sample 2 | 5.9 | 65 | 0.170 | 440 |
| Control sample 3 | 16.3 | 90 | 0.189 | 710 |
| Control sample 4 | 15.1 | 90 | 0.177 | 720 |

| Sample No. | Odor |
|---|---|
| Test sample 1 | No odor |
| Test sample 2 | No odor |
| Control sample 1 | No odor |
| Control sample 2 | No odor |

As shown above, sodium hydroxylauryl ether carboxylate and potassium hydroxylauryl ether carboxylate are harder to foam at pH 4. On the other hand, the sodium hypotaurate salt of a hydroxylauryl ether carboxylic acid of the present invention and triethanolamine or a lysine salt of a hydroxylauryl ether carboxylic acid foam well at a more acidic pH. However, the detergent compositions of the present invention are also shown to be superior in terms of the creaminess and durability of the foam, compared with the triethanolamine hydroxylauryl ether carboxylate and lysine hydroxylauryl ether carboxylate.

Also, the alkali metal hypotaurate salt of a hydroxylauryl ether carboxylic acid and the organic alkali hypotaurate of a hydroxylauryl ether carboxylic acid of the present invention are salts of a hydroxy-fatty acid and a weak base and yet, similar to alkali metal salts and alkali earth metal salts of a hydroxy-fatty acid, they don't have an offensive odor.

TABLE 20

| Sample name | Sample No. |
|---|---|
| Sodium N-methyltaurate lauroylalanine | Test sample 1 |
| Triethanolamine taurate lauroylalanine | Test sample 2 |
| Sodium lauroylalanine | Control sample 1 |
| Potassium lauroylalanine | Control sample 2 |
| Triethanolamine lauroylalanine | Control sample 3 |
| Lysine salt of lauroylalanine | Control sample 4 |

TABLE 20-continued

| Sample No. | Foam height (cm) | Foam film thickness (µ) | Foam density (g/ml) | Duration (min.) |
|---|---|---|---|---|
| Test sample 1 | 9.8 | 105 | 0.200 | 830 |
| Test sample 2 | 10.7 | 110 | 0.210 | 880 |
| Control sample 1 | 7.1 | 60 | 0.163 | 430 |
| Control sample 2 | 6.9 | 65 | 0.170 | 440 |
| Control sample 3 | 6.3 | 85 | 0.179 | 450 |
| Control sample 4 | 6.5 | 85 | 0.177 | 400 |

| Sample No. | Odor |
|---|---|
| Test sample 1 | No odor |
| Test sample 2 | No odor |
| Control sample 1 | No odor |
| Control sample 2 | No odor |

As shown above, sodium lauroylalanine and potassium lauroylalanine are harder to foam at pH 7. On the other hand, sodium taurate and/or N-methyltaurate salt of lauroylalanine of the present invention and triethanolamine and/or lysine salt of a lauroylalanine foam well at a more acidic pH. However, compared with triethanolamine lauroylalanine and lysine lauroylalanine, the detergent compositions of the present invention are shown to be superior in terms of the creaminess and durability of the foam.

Also, the alkali metal taurate and/or N-methyltaurate salt of lauroylalanine and the organic alkali taurate and/or N-methyltaurate salt of lauroylalanine of the present invention are salts of a weak acid and a weak base and yet, similar to alkali metal salts or alkali earth metal salts, they don't have an offensive odor.

TABLE 21

| Sample name | Sample No. |
|---|---|
| Sodium hypotaurate lauroylalanine | Test sample 1 |
| Triethanolamine hypotaurate lauroylalanine | Test sample 2 |
| Sodium lauroylalanine | Control sample 1 |
| Potassium lauroylalanine | Control sample 2 |
| Triethanolamine lauroylalanine | Control sample 3 |
| Lysine salt of lauroylalanine | Control sample 4 |

| Sample No. | Foam height (cm) | Foam film thickness (µ) | Foam density (g/ml) | Duration (min.) |
|---|---|---|---|---|
| Test sample 1 | 9.2 | 100 | 0.195 | 810 |
| Test sample 2 | 10.5 | 105 | 0.205 | 870 |
| Control sample 1 | 7.1 | 60 | 0.163 | 430 |
| Control sample 2 | 6.9 | 65 | 0.170 | 440 |
| Control sample 3 | 6.3 | 85 | 0.179 | 450 |
| Control sample 4 | 6.5 | 85 | 0.177 | 400 |

| Sample No. | Odor |
|---|---|
| Test sample 1 | No odor |
| Test sample 2 | No odor |
| Control sample 1 | No odor |
| Control sample 2 | No odor |

As shown above, sodium lauroylalanine and potassium lauroylalanine are harder to foam at pH 7. On the other hand, sodium hypotaurate salt of lauroylalanine of the present invention and triethanolamine and/or lysine salt of a lauroylalanine foam well at a more acidic pH. However, compared with triethanolamine lauroylalanine and lysine salt of lauroylalanine, the detergent compositions of the present invention are shown to be superior in terms of the creaminess and durability of the foam.

Also, the alkali metal hypotaurate salt of lauroylalanine and the organic alkali hypotaurate salt of lauroylalanine of the present invention are salts of a weak acid and a weak base and yet, similar to alkali metal salts or alkali earth metal salts, they don't have an offensive odor.

In the same manner as described above, sodium taurate, N-methyltaurate or hypotaurate salt or triethanol amine taurate, N-methyltaurate or hypotaurate salt of POE (2) lauryl ether carboxylic acid, glycerine lauryl ether carboxylic acid and lauroylacetic acid were tested by a foaming test with the shaking method and a sensory test of the odor. All of them foamed well even on the acidic side, were superior in terms of the creaminess of the foam and the durability of the foam and had no odor, making them superior ingredients for a detergent composition.

[Sensory Test of Actual Use]

Fifty panelists were used to conduct the actual use test for test samples shown in the following tables. The test of actual use was conducted as follows. 10 ml of a 10% aqueous solution of each sample was put on a hand and the hand was washed for 30 seconds. The feeling during use and after rinsing was rated with a five point scale based on the criteria shown below. The average of the fifty panelists was calculated to obtain the total evaluation. The results are shown in the following tables.

TABLE 22

| | Evaluation Point | | | | |
|---|---|---|---|---|---|
| Item | 5 | 4 | 3 | 2 | 1 |
| Foaming | Very good | Somewhat good | Normal | Somewhat poor | Very poor |
| Creaminess of the foam | Very good | Somewhat good | Normal | Somewhat poor | Very poor |
| Refreshing feeling after use | Very refreshing | Somewhat refreshing | Normal | Somewhat slimy | Very slimy |
| Moist feeling after drying | Very moist | Somewhat moist | Normal | Somewhat stretched | Very stretched |

⊚: The average of the evaluation points is 4–5.
o: The average of the evaluation points is 3–3.9.
Δ: The average of the evaluation points is 2–2.9.
x: The average of the evaluation points is 1–1.9.

(Various Samples and the Comprehensive Evaluation of Them)

TABLE 23

| Sample name | Sample No. |
|---|---|
| Sodium N-methyltaurate hydroxylaurate | Test sample 1 |
| Triethanolamine taurate hydroxylaurate | Test sample 2 |
| Sodium hydroxylaurate | Control sample 1 |
| Triethanolamine hydroxylaurate | Control sample 2 |
| Sodium lauroylmethyl taurate | Control sample 3 |

| Sample No. | Foaming | Creaminess of the foam | Refreshing feeling after use | Moist feeling after drying |
|---|---|---|---|---|
| Test sample 1 | ⊚ | ⊚ | ⊚ | ⊚ |
| Test sample 2 | ⊚ | ⊚ | o | ⊚ |
| Control sample 1 | ⊚ | o | ⊚ | x |
| Control sample 2 | o | o | Δ | ⊚ |
| Control sample 3 | o | o | x | ⊚ |

TABLE 24

| Sample name | Sample No. |
|---|---|
| Sodium hypotaurate hydroxylaurate | Test sample 1 |
| Triethanolamine hypotaurate hydroxylaurate | Test sample 2 |
| Sodium hydroxylaurate | Control sample 1 |
| Triethanolamine hydroxylaurate | Control sample 2 |
| Sodium lauroylmethyl taurate | Control sample 3 |

| Sample No. | Foaming | Creaminess of the foam | Refreshing feeling after use | Moist feeling after drying |
|---|---|---|---|---|
| Test sample 1 | ⊚ | ⊚ | ⊚ | ⊚ |
| Test sample 2 | ⊚ | ⊚ | ⊚ | ⊚ |
| Control sample 1 | ⊚ | o | ⊚ | x |
| Control sample 2 | o | o | Δ | ⊚ |
| Control sample 3 | o | o | x | ⊚ |

TABLE 25

| Sample name | Sample No. |
|---|---|
| Sodium N-methyltaurate hydroxylauryl ether carboxylate | Test sample 1 |
| Triethanolamine taurate hydroxylauryl ether carboxylate | Test sample 2 |
| Sodium hydroxylauryl ether carboxylate | Control sample 1 |
| Triethanolamine hydroxylauryl ether carboxylate | Control sample 2 |
| Sodium lauroylmethyl taurate | Control sample 3 |

| Sample No. | Foaming | Creaminess of the foam | Refreshing feeling after use | Moist feeling after drying |
|---|---|---|---|---|
| Test sample 1 | ⊚ | ⊚ | ⊚ | ⊚ |
| Test sample 2 | ⊚ | ⊚ | o | ⊚ |
| Control sample 1 | ⊚ | o | ⊚ | x |
| Control sample 2 | ⊚ | o | Δ | Δ |
| Control sample 3 | o | o | x | ⊚ |

TABLE 26

| Sample name | Sample No. |
| --- | --- |
| Sodium hypotaurate hydroxylauryl ether carboxylate | Test sample 1 |
| Triethanolamine hypotaurate hydroxylauryl ether carboxylate | Test sample 2 |
| Sodium hydroxylauryl ether carboxylate | Control sample 1 |
| Triethanolamine hydroxylauryl ether carboxylate | Control sample 2 |
| Sodium lauroylmethyl taurate | Control sample 3 |

| Sample No. | Foaming | Creaminess of the foam | Refreshing feeling after use | Moist feeling after drying |
| --- | --- | --- | --- | --- |
| Test sample 1 | ⊙ | ⊙ | ⊙ | ⊙ |
| Test sample 2 | ⊙ | ⊙ | ○ | ⊙ |
| Control sample 1 | ⊙ | ○ | ⊙ | x |
| Control sample 2 | ⊙ | ○ | Δ | Δ |
| Control sample 3 | ○ | ○ | x | ⊙ |

TABLE 27

| Sample name | Sample No. |
| --- | --- |
| Sodium taurate lauroylalanine | Test sample 1 |
| Triethanolamine N-methyltaurate lauroylalanine | Test sample 2 |
| Sodium lauroylalanine | Control sample 1 |
| Triethanolamine lauroylalanine | Control sample 2 |
| Sodium lauroylmethyl taurate | Control sample 3 |

| Sample No. | Foaming | Creaminess of the foam | Refreshing feeling after use | Moist feeling after drying |
| --- | --- | --- | --- | --- |
| Test sample 1 | ⊙ | ○ | ⊙ | ⊙ |
| Test sample 2 | ⊙ | ○ | ○ | ⊙ |
| Control sample 1 | ○ | Δ | ○ | ○ |
| Control sample 2 | ○ | Δ | x | ○ |
| Control sample 3 | ○ | ○ | x | ⊙ |

TABLE 28

| Sample name | Sample No. |
| --- | --- |
| Sodium hypotaurate lauroylalanine | Test sample 1 |
| Triethanolamine hypotaurate lauroylalanine | Test sample 2 |
| Sodium lauroylalanine | Control sample 1 |
| Triethanolamine lauroylalanine | Control sample 2 |
| Sodium lauroylmethyl taurate | Control sample 3 |

| Sample No. | Foaming | Creaminess of the foam | Refreshing feeling after use | Moist feeling after drying |
| --- | --- | --- | --- | --- |
| Test sample 1 | ⊙ | ○ | ○ | ⊙ |
| Test sample 2 | ⊙ | ○ | ○ | ⊙ |
| Control sample 1 | ○ | Δ | ○ | ○ |
| Control sample 2 | ○ | Δ | x | ○ |
| Control sample 3 | ○ | ○ | x | ⊙ |

Comparison between samples in the comprehensive evaluation tables with the same alkali portion indicates that insertion of taurine, N-methyltaurine or hypotaurine in the structure improves all the feelings during use. The reason why an amphoteric compound which has both strong acid and weak base (—$NH_2$) functional groups, such as taurine, N-methyltaurine or hypotaurine, has the aforementioned effects is believed to be as follows: during washing when there is plenty of water, the —$COO^-$ group of the fatty acid dissociates to give a feeling close to sodium soap, whereas after use when it is dry and there is not much water, the —$COO^-$ group of the fatty acid forms an ion pair with the $N^+$ portion of taurine or N-methyltaurine and the melting point of the hydrated crystal, dependent on the concentration, rises to cause insolubility in water and produce the feeling of use of sulfonic acid type surfactants.

In the same manner as described above, sodium taurate, N-methyltaurate or hypotaurate salt or triethanol amine taurate, N-methyltaurate or hypotaurate salt of POE (2) lauryl ether carboxylic acid, glycerine lauryl ether carboxylic acid and lauroylacetic acid were tested by the same test of actual use and all of them exhibited a superior feeling during use.

Examples of the detergent composition of the present invention which contain an alkali metal taurine, N-methyltaurate or hypotaurine salt or organic alkali taurine, N-methyltaurate or hypotaurine salt of various organic acids are described below. The blend ratios are expressed in weight percent units.

Example 1

Shampoo

| | wt % |
| --- | --- |
| (1) Ethylene glycol fatty acid ester | 2.0 |
| (2) Triethanolamine N-methyltaurate hydroxylaurate | 10.0 |
| (3) Dodecyl maltoside | 5.0 |
| (4) Laurylsulfobetaine | 10.0 |
| (5) Sodium lauroyl hydrolyzed silk peptide | 5.0 |
| (6) Propylene glycol | 2.0 |
| (7) Coloring agent, perfume | Appropriate amount |
| (8) Purified water | Balance |

(Preparation Method)

Preparation was carried out according to the conventional method.

The shampoo of the present invention exhibited a lower irritation to hair and scalp, superior foaming properties, no stickiness and superior feeling during use.

Also, the shampoos of the present invention for which (2) Triethanolamine N-methyltaurate hydroxylaurate was replaced by the same amount of one or more types chosen from among sodium taurate, N-methyltaurate or hypotaurate salt or triethanol amine taurate, N-methyltaurate or hypotaurate salt of hydroxylauric acid, lauroylalanine, POE (2) lauryl ether carboxylic acid, glycerine lauryl ether carboxylic acid and lauroylacetic acid exhibited similar effects.

Example 2

Shampoo

|  | wt % |
|---|---|
| (1) Sodium cocoylmethyl taurate | 8.0 |
| (2) Triethanolamine taurate salt of hydroxylauric acid | 20.0 |
| (3) Sodium N-methyltaurate salt of myristic acid | 2.0 |
| (4) Diethanol amide of coconut fatty acid | 4.0 |
| (5) Perfume | Appropriate amount |
| (6) EDTA.2Na | Appropriate amount |
| (7) Purified water | Balance |

(Preparation Method)

Preparation was carried out according to the conventional method.

The shampoo of the present invention exhibited a lower irritation to hair and scalp, superior foaming properties, no stickiness and superior feeling during use.

Also, the shampoos of the present invention for which (2) Triethanolamine taurate salt of hydroxylauric acid was replaced by the same amount of one or more types chosen from among sodium taurate, N-methyltaurate or hypotaurate salt or triethanol amine taurate, N-methyltaurate or hypotaurate salt of hydroxylauric acid, hydroxymyristyl ether carboxylic acid, lauroylglycine., POE (2) lauryl ether carboxylic acid, glycerine lauryl ether carboxylic acid and lauroylacetic acid exhibited similar effects.

Example 3

Body Shampoo

|  | wt % |
|---|---|
| (1) Glycerine | 5.0 |
| (2) Potassium taurate salt of hydroxymyristic acid | 5.0 |
| (3) Myristic ester of sucrose | 1.0 |
| (4) Triethanolamine lauryl ether carboxylate | 10.0 |
| (5) Sodium laurylsulfonsuccinate | 5.0 |
| (6) Diethanol amide of coconut oil | 3.0 |
| (7) Chelating agent | 0.1 |
| (8) Coloring agent, perfume | Appropriate amount |
| (9) Purified water | Balance |

(Preparation Method)

Preparation was carried out according to the conventional method.

The body shampoo of the present invention exhibited a lower irritation to skin, excellent foaming during use, and a moist feeling after washing was completed.

Also, the body shampoos of the present invention for which (2) Potassium taurate salt of hydroxymyristic acid was replaced by the same amount of one or more types chosen from among sodium taurate, N-methyltaurate or hypotaurate salt or triethanol amine taurate, N-methyltaurate or hypotaurate salt of hydroxymyristic acid, hydroxymyristyl ether carboxylic acid, palmitoylglutamic acid, POE (2) lauryl ether carboxylic acid, glycerine lauryl ether carboxylic acid and lauroylacetic acid exhibited similar effects.

Example 4

Body Shampoo

|  | wt % |
|---|---|
| (1) Sorbitol | 2.0 |
| (2) Erythritol | 5.0 |
| (3) Octyl glucoside | 15.0 |
| (4) Sodium N-methyltaurate salt of hydroxypalmitic acid | 5.0 |
| (5) Diethanol amine hypotaurate of coconut oil | 3.0 |
| (6) Chelating agent | 0.1 |
| (7) Cationized cellulose | 0.2 |
| (8) Coloring agent, perfume | Appropriate amount |
| (9) Purified water | Balance |

(Preparation Method)

Preparation was carried out according to the conventional method.

The body shampoo of the present invention exhibited a lower irritation to skin, excellent foaming during use, and a moist feeling after washing was completed.

Also, the body shampoos of the present invention for which (4) Sodium N-methyltaurate salt of palmitic acid was replaced by the same amount of one or more types chosen from among sodium taurate, N-methyltaurate or hypotaurate salt or triethanol amine taurate, N-methyltaurate or hypotaurate salt of hydroxypalmitic acid, hydroxystearyl ether carboxylic acid, stearoylalanine, POE (2) lauryl ether carboxylic acid, glycerine lauryl ether carboxylic acid and lauroylacetic acid exhibited similar effects.

Example 5

Liquid Detergent for Clothes

|  | wt % |
|---|---|
| (1) Sodium hypotaurate POE (3 moles) lauryl ether sulfate | 10.0 |
| (2) Maltotritol dodecyl ether | 30.0 |
| (3) Lysine taurate salt of hydroxystearic acid | 15.0 |
| (4) Distearyldimethylammonium chloride | 2.0 |
| (5) Aprotinin | 0.5 |
| (6) Bleach | Appropriate amount |
| (7) Purified water | Balance |

(Preparation Method)

Preparation was carried out according to the conventional method.

The detergent for clothes of the present invention was highly safe and had a superior cleaning capability.

Also, the liquid detergents for clothes of the present invention for which (3) Lysine taurate salt of hydroxystearic acid was replaced by the same amount of one or more types chosen from among sodium taurate, N-methyltaurate or hypotaurate salt or triethanol amine taurate, N-methyltaurate or hypotaurate salt of hydroxystearic acid, hydroxylauryl ether carboxylic acid, lauroylglycine, POE (2) lauryl ether carboxylic acid, glycerine lauryl ether carboxylic acid and lauroylacetic acid exhibited similar effects.

Example 6
Powder Detergent for Clothes

|  | wt % |
|---|---|
| (1) LAS-Na | 15.0 |
| (2) Sodium N-methyltaurate salt of castor oil hydroxy fatty acid | 1.0 |
| (3) Sodium taurate lauroylglycine | 3.0 |
| (4) Na$_2$SO$_4$ | 30.0 |
| (5) 2-phenylacetamide | 2.0 |
| (6) CMC (66%) | 1.5 |
| (7) Metasilicic soda (anhydride) | 20.0 |
| (8) Fluorescent whitening agent | 0.2 |
| (9) Na$_2$CO$_3$ | Balance |

(Preparation Method)

Preparation was carried out according to the conventional method.

The powder detergent for clothes of the present invention was highly safe and had a superior cleaning capability.

Also, the powder detergents for clothes of the present invention for which (2) Sodium N-methyltaurate salt of castor oil hydroxy fatty acid was replaced by the same amount of one or more types chosen from among sodium taurate, N-methyltaurate or hypotaurate salt or triethanol amine taurate, N-methyltaurate or hypotaurate salt of castor oil hydroxy fatty acid, hydroxylauryl ether carboxylic acid, lauroylalanine, POE (2) lauryl ether carboxylic acid, glycerine lauryl ether carboxylic acid and lauroylacetic acid exhibited similar effects.

Example 7
Solid Soap

|  | wt % |
|---|---|
| (1) Beef tallow | 20.0 |
| (2) Coconut oil | 12.0 |
| (3) Castor oil | 5.0 |
| (4) Olive oil | 3.0 |
| (5) Sodium N-methyltaurate | 6.0 |
| (6) Ethanol | 20.0 |
| (7) Maltitolhydroxyhexadecyl ether | 4.0 |
| (8) Sodium taurate salt of lanoline hydroxy fatty acid | 1.0 |
| (9) Glycerine | 5.0 |
| (10) Sucrose | 10.0 |
| (11) Cyclohexylguanidine | 3.0 |
| (12) EDTA | 0.1 |
| (13) Perfume | Appropriate amount |
| (14) Pigment | Appropriate amount |
| (15) Purified water | Balance |

(Preparation Method)

Preparation was carried out according to the conventional method.

The solid soap of the present invention exhibited a lower irritation to skin, excellent foaming during use, and a refreshing feeling after washing was completed.

Also, the solid soaps of the present invention for which (8) Sodium taurate salt of lanoline hydroxy fatty acid was replaced by the same amount of one or more types chosen from among sodium taurate, N-methyltaurate or hypotaurate salt or triethanol amine taurate, N-methyltaurate or hypotaurate salt of lanoline hydroxy fatty acid, hydroxyisostearyl ether carboxylic acid, isostearoylglycine, POE (2) lauryl ether carboxylic acid, glycerine lauryl ether carboxylic acid and lauroylacetic acid exhibited similar effects.

Example 8
Liquid Soap

|  | wt % |
|---|---|
| (1) Lauric acid | 3.0 |
| (2) Myristic acid | 7.0 |
| (3) Palmitic acid | 3.0 |
| (4) Oleic acid | 2.5 |
| (5) Lauroyldiethanolamide | 6.0 |
| (6) Propylene glycol | 11.0 |
| (7) Erythritol | 4.0 |
| (8) Sodium N-methyltaurate salt of hydroxydecanoic acid | 10.0 |
| (9) Triethanolamine taurate salt of lauric acid | 3.0 |
| (10) Sucrose | 5.0 |
| (11) Sodium hydroxide | 3.0 |
| (12) EDTA | 0.1 |
| (13) p-aminobenzamidine | 1.0 |
| (14) Perfume | Appropriate amount |
| (15) Purified water | Balance |

(Preparation Method)

Preparation was carried out according to the conventional method.

The liquid soap of the present invention exhibited a lower irritation to skin, excellent foaming during use, and a refreshing feeling after washing was completed.

Also, the liquid soaps of the present invention for which (8) Sodium N-methyltaurate salt of hydroxydecanoic acid was replaced by the same amount of one or more types chosen from among sodium taurate, N-methyltaurate or hypotaurate salt or triethanol amine taurate, N-methyltaurate or hypotaurate salt of hydroxydecane fatty acid, hydroxylauryl ether carboxylic acid, lauroylalanine, POE (2) lauryl ether carboxylic acid, glycerine lauryl ether carboxylic acid and lauroylacetic acid exhibited similar effects.

5. Examples of Claims 21–23

[The Foaming Test with the Shaking Method and the Sensory Test of the Odor]

0.5 wt % of each detergent was dissolved in ion exchanged water with. 70 ppm calcium chloride already dissolved in it. The pH was then adjusted to 7.0. This solution was kept at 30$20$ C., put into a Nessler's tube with an inner diameter of 3 cm and a height of 20 cm equipped with a sliding plug, and then tilted 90 degrees every second using a pendulum type shaker. After one minute, the sample was taken out of the shaker and the foam height, the foam film thickness and the foam density were measured. The time required for the foam height to be reduced to a half of the original height was also measured. The foam film thickness was measured by taking a photograph of the foam using a microscope at 100 times magnification and calculating the average value on the photograph. The foam density was obtained by sampling 10 ml of the foam and measuring its weight. The test samples and the measurement results are shown in the following tables. In the aforementioned foaming test with the shaking method, the foam height relates to how good the foaming is, the foam film thickness and the foam density relate to the creaminess of the foam, and the duration relates to the durability of the foam at the time of use. A larger value indicates a better performance.

TABLE 29

| Sample name | Sample No. |
|---|---|
| Sodium taurate salt of lauroyl hydrolyzed silk peptide | Test sample 1 |
| Triethanolamine N-methyltaurate salt of lauroyl hydrolized soybean protein | Test sample 2 |
| Sodium salt of lauroyl hydrolyzed silk peptide | Control sample 1 |
| Potassium salt of lauroyl hydrolyzed collagen | Control sample 2 |
| Magnesium salt of lauroyl hydrolyzed collagen | Control sample 3 |
| Triethanolamine salt of lauroyl hydrolyzed soybean protein | Control sample 4 |
| Lysine salt of lauroyl hydrolyzed wheat protein | Control sample 5 |

| Sample No. | Foam height (cm) | Foam film thickness ($\mu$) | Foam density (g/ml) | Duration (min.) |
|---|---|---|---|---|
| Test sample 1 | 9.8 | 115 | 0.210 | 830 |
| Test sample 2 | 11.3 | 105 | 0.215 | 890 |
| Control sample 1 | 6.7 | 80 | 0.173 | 410 |
| Control sample 2 | 6.1 | 65 | 0.171 | 450 |
| Control sample 3 | 4.1 | 70 | 0.105 | 110 |
| Control sample 4 | 7.3 | 85 | 0.170 | 490 |
| Control sample 5 | 7.7 | 85 | 0.170 | 410 |

TABLE 30

| Sample name | Sample No. |
|---|---|
| Sodium hypotaurate salt of lauroyl hydrolyzed silk peptide | Test sample 1 |
| Triethanolamine hypotaurate salt of lauroyl hydrolyzed soybean protein | Test sample 2 |
| Sodium salt of lauroyl hydrolyzed silk peptide | Control sample 1 |
| Potassium salt of lauroyl hydrolyzed collagen | Control sample 2 |
| Magnesium salt of lauroyl hydrolyzed collagen | Control sample 3 |
| Triethanolamine salt of lauroyl hydrolyzed soybean protein | Control sample 4 |
| Lysine salt of lauroyl hydrolyzed wheat protein | Control sample 5 |

| Sample No. | Foam height (cm) | Foam film thickness ($\mu$) | Foam density (g/ml) | Duration (min.) |
|---|---|---|---|---|
| Test sample 1 | 9.5 | 110 | 0.215 | 820 |
| Test sample 2 | 11.0 | 100 | 0.210 | 870 |
| Control sample 1 | 6.7 | 80 | 0.173 | 410 |
| Control sample 2 | 6.1 | 65 | 0.171 | 450 |
| Control sample 3 | 4.1 | 70 | 0.105 | 110 |
| Control sample 4 | 7.3 | 85 | 0.170 | 490 |
| Control sample 5 | 7.7 | 85 | 0.170 | 410 |

As shown above, sodium salt of lauroyl hydrolyzed silk peptide, potassium salt of lauroyl hydrolyzed collagen and magnesium salt of lauroyl hydrolyzed collagen are harder to foam at pH 7.

On the other hand, sodium taurate salt of lauroyl hydrolyzed silk peptide and triethanolamine N-methyltaurate salt of lauroyl hydrolyzed soybean protein of the present invention, as well as triethanolamine salt of lauroyl hydrolyzed soybean protein, lysine salt of lauroyl hydrolyzed wheat protein, sodium hypotaurate salt of lauroyl hydrolyzed silk peptide, triethanolamine hypotaurate salt of lauroyl hydrolyzed soybean protein, triethanolamine salt of lauroyl hydrolyzed soybean protein and lysine salt of lauroyl hydrolyzed wheat protein foam well at a more acidic pH. However, the detergent compositions of the present invention are shown to be superior in terms of the creaminess and durability of the foam compared with triethanolamine salt of lauroyl hydrolyzed soybean protein and lysine salt of lauroyl hydrolyzed wheat protein.

[Sensory Test of Actual Use]

Fifty panelists were used to conduct the actual use test for test samples shown in the following tables. The test of actual use was conducted as follows. 10 ml of a 10% aqueous solution of each sample was put on a hand and the hand was washed for 30 seconds. The feeling during use and after rinsing was rated with a five point scale based on the criteria shown below. The average of the fifty panelists was calculated to obtain the total evalution. The results are shown in the following tables.

(Evaluation Criteria)

TABLE 31

| | Evaluation Point | | | | |
|---|---|---|---|---|---|
| Item | 5 | 4 | 3 | 2 | 1 |
| Foaming | Very good | Somewhat good | Normal | Somewhat poor | Very poor |
| Creaminess of the foam | Very good | Somewhat good | Normal | Somewhat poor | Very poor |
| Refreshing feeling after use | Very refreshing | Somewhat refreshing | Normal | Somewhat slimy | Very slimy |
| Moist feeling after drying | Very moist | Somewhat moist | Normal | Somewhat stretched | Very stretched |

⊚: The average of the evaluation points is 4–5.
o: The average of the evaluation points is 3–3.9.
Δ: The average of the evaluation points is 2–2.9.
x: The average of the evaluation points is 1–1.9.

(Various Samples and the Comprehensive Evaluation of Them)

TABLE 32

| Sample name | Sample No. |
|---|---|
| Sodium taurate salt of lauroyl hydrolyzed silk peptide | Test sample 1 |
| Triethanolamine N-methyltaurate salt of lauroyl hydrolyzed soybean protein | Test sample 2 |
| Sodium salt of lauroyl hydrolyzed silk peptide | Control sample 1 |
| Magnesium salt of lauroyl hydrolyzed collagen | Control sample 2 |
| Triethanolamine salt of lauroyl hydrolyzed soybean protein | Control sample 3 |
| Sodium taurate salt of lauroyl hydrolyzed wheat protein | Control sample 4 |

TABLE 32-continued

| Sample No. | Foaming | Creaminess of the foam | Refreshing feeling after use | Moist feeling after drying |
|---|---|---|---|---|
| Test sample 1 | ◎ | ◎ | ◎ | ◎ |
| Test sample 2 | ◎ | ◎ | ◎ | ◎ |
| Control sample 1 | ○ | Δ | ○ | ○ |
| Control sample 2 | Δ | x | ○ | ○ |
| Control sample 3 | ○ | Δ | x | ○ |
| Control sample 4 | ○ | ○ | x | ◎ |

(Various Samples and the Comprehensive Evaluation of Them)

TABLE 33

| Sample name | Sample No. |
|---|---|
| Sodium hypotaurate salt of lauroyl hydrolyzed silk peptide | Test sample 1 |
| Triethanolamine hypotaurate salt of lauroyl hydrolyzed soybean protein | Test sample 2 |
| Sodium salt of lauroyl hydrolyzed silk peptide | Control sample 1 |
| Magnesium salt of lauroyl hydrolyzed collagen | Control sample 2 |
| Triethanolamine salt of lauroyl hydrolyzed soybean protein | Control sample 3 |
| Lysine salt of lauroyl hydrolyzed wheat protein | Control sample 4 |

| Sample No. | Foaming | Creaminess of the foam | Refreshing feeling after use | Moist feeling after drying |
|---|---|---|---|---|
| Test sample 1 | ◎ | ○ | ◎ | ◎ |
| Test sample 2 | ◎ | ○ | ○ | ◎ |
| Control sample 1 | ○ | Δ | ○ | ○ |
| Control sample 2 | Δ | x | ○ | ○ |
| Control sample 3 | ○ | Δ | x | ○ |
| Control sample 4 | ○ | ○ | x | ◎ |

Comparison between samples in the comprehensive evaluation tables with the same alkali portion indicates that insertion of taurine, N-methyltaurine or hypotaurine in the structure improves all the feelings during use. The reason why an amphoteric compound which has both strong acid and weak base (–NH$_2$) functional groups, such as taurine, N-methyltaurine or hypotaurine, has the aforementioned effects is believed to be as follows: during washing when there is plenty of water, the —COO$^-$ group of the fatty acid dissociates to give a feeling close to sodium soap, whereas after use when it is dry and there is not much water, the —COO$^-$ group of the fatty acid forms an ion pair with the N$^+$ portion of taurine or N-methyltaurine and the melting point of the hydrated crystal, dependent on the concentration, rises to cause insolubility in water and produce the feeling of use of sulfonic acid type surfactants.

Examples of the detergent composition of the present invention which contain an alkali metal taurine, N-methyltaurate or hypotaurine salt or organic alkali taurine, N-methyltaurate or hypotaurine salt of acylated peptides are described below. The blend ratios are expressed in weight percent units.

Example 1

Shampoo

| | | wt % |
|---|---|---|
| (1) | Ethylene glycol coconut oil fatty acid ester | 2.0 |
| (2) | Triethanolamine taurate salt of lauroyl hydrolyzed silk peptide | 10.0 |
| (3) | Dodecyl maltoside | 5.0 |
| (4) | Laurylsulfobetaine | 10.0 |
| (5) | Diethanolamine taurate laurate | 5.0 |
| (6) | Propylene glycol | 2.0 |
| (7) | Coloring agent, perfume | Appropriate amount |
| (8) | Purified water | Balance |

(Preparation Method)

Preparation was carried out according to the conventional method.

The shampoo of the present invention exhibited a lower irritation to hair and scalp, superior foaming properties, no stickiness and superior feeling during use.

Example 2

Shampoo

| | | wt % |
|---|---|---|
| (1) | Sodium cocylmethyl taurate | 8.0 |
| (2) | Sodium N-methyltaurate salt of lauroyl hydrolyzed collagen | 20.0 |
| (3) | Sodium hypotaurate salt of myristic acid | 2.0 |
| (4) | Diethanol amide of coconut fatty acid | 4.0 |
| (5) | Perfume | Appropriate amount |
| (6) | EDTA · 2Na | Appropriate amount |
| (7) | Purified water | Balance |

(Preparation Method)

Preparation was carried out according to the conventional method.

The shampoo of the present invention exhibited a lower irritation to hair and scalp, superior foaming properties, no stickiness and superior feeling during use.

Example 3

Body Shampoo

| | | wt % |
|---|---|---|
| (1) | Glycerine | 5.0 |
| (2) | Potassium taurate salt of palmitoyl hydrolyzed wheat protein | 5.0 |
| (3) | Myristic ester of sucrose | 1.0 |
| (4) | Potassium N-methyltaurate laurate | 10.0 |
| (5) | Sodium laurylsulfonsuccinate | 5.0 |
| (6) | Diethanol amide of coconut oil | 3.0 |
| (7) | Chelating agent | 0.1 |
| (8) | Coloring agent, perfume | Appropriate amount |
| (9) | Purified water | Balance |

(Preparation Method)

Preparation was carried out according to the conventional method.

The body shampoo of the present invention exhibited a lower irritation to skin, excellent foaming during use, and a moist feeling after washing was completed.

Example 4
Body Shampoo

|  |  | wt % |
|---|---|---|
| (1) | Sorbitol | 2.0 |
| (2) | Erythritol | 5.0 |
| (3) | Potassium N-methyltaurate α-hydroxy-laurate | 15.0 |
| (4) | Sodium N-methyltaurate salt of stearoyl hydrolyzed soybean protein | 5.0 |
| (5) | Diethanol amide of coconut oil | 3.0 |
| (6) | Chelating agent | 0.1 |
| (7) | Cationized cellulose | 0.2 |
| (8) | Coloring agent, perfume | Appropriate amount |
| (9) | Purified water | Balance |

(Preparation Method)

Preparation was carried out according to the conventional method.

The body shampoo of the present invention exhibited a lower irritation to skin, excellent foaming during use, and a moist feeling after washing was completed.

Example 5
Liquid Detergent for Clothes

|  |  | wt % |
|---|---|---|
| (1) | Sodium POE (3 moles) lauryl ether sulfate | 10.0 |
| (2) | Maltotritol hydroxydodecyl ether | 30.0 |
| (3) | Lysine taurate salt of lauryl hydrolyzed collagen | 15.0 |
| (4) | Sodium taurate laurate | 2.0 |
| (5) | Aprotinin | 0.5 |
| (6) | Bleach | Appropriate amount |
| (7) | Purified water | Balance |

(Preparation Method)

Preparation was carried out according to the conventional method.

The detergent for clothes of the present invention was highly safe and had a superior cleaning capability.

Example 6
Powder Detergent for Clothes

|  |  | wt % |
|---|---|---|
| (1) | LAS-Na | 15.0 |
| (2) | Sodium taurate salt of lauroyl hydrolyzed soybean protein | 1.0 |
| (3) | Octyl glucoside | 3.0 |
| (4) | $Na_2SO_4$ | 30.0 |
| (5) | 2-phenylacetamide | 2.0 |
| (6) | CMC (66%) | 1.5 |
| (7) | Metasilicic soda (anhydride) | 20.0 |
| (8) | Fluorescent whitening agent | 0.2 |
| (9) | $Na_2CO_3$ | Balance |

(Preparation Method)

Preparation was carried out according to the conventional method.

The powder detergent for clothes of the present invention was highly safe and had a superior cleaning capability.

Example 7
Solid Soap

|  |  | wt % |
|---|---|---|
| (1) | Beef tallow | 20.0 |
| (2) | Coconut oil | 12.0 |
| (3) | Castor oil | 5.0 |
| (4) | Olive oil | 3.0 |
| (5) | Sodium taurate | 6.0 |
| (6) | Ethanol | 20.0 |
| (7) | Maltitolhydroxyhexadecyl ether | 4.0 |
| (8) | Sodium taurate salt of isostearoyl hydrolyzed soybean protein | 1.0 |
| (9) | Glycerine | 5.0 |
| (10) | Sucrose | 10.0 |
| (11) | Cyclohexylguanidine | 3.0 |
| (12) | EDTA | 0.1 |
| (13) | Perfume | Appropriate amount |
| (14) | Pigment | Appropriate amount |
| (15) | Purified water | Balance |

(Preparation Method)

Preparation was carried out according to the conventional method.

The solid soap of the present invention exhibited a lower irritation to skin, excellent foaming during use, and a refreshing feeling after washing was completed.

Example 8
Liquid Soap

|  |  | wt % |
|---|---|---|
| (1) | Lauric acid | 3.0 |
| (2) | Myristic acid | 7.0 |
| (3) | Palmitic acid | 3.0 |
| (4) | Oleic acid | 2.5 |
| (5) | Lauroyldiethanolamide | 6.0 |
| (6) | Propylene glycol | 11.0 |
| (7) | Erythritol | 4.0 |
| (8) | Sodium hypotaurate salt of lauroyl hydrolyzed collagen | 10.0 |
| (9) | Triethanolamine taurate laurate | 3.0 |
| (10) | Sucrose | 5.0 |
| (11) | Sodium hydroxide | 3.0 |
| (12) | EDTA | 0.1 |
| (13) | p-aminobenzamidine | 1.0 |
| (14) | Perfume | Appropriate amount |
| (15) | Purified water | Balance |

(Preparation Method)

Preparation was carried out according to the conventional method.

The liquid soap of the present invention exhibited a lower irritation to skin, excellent foaming during use, and a refreshing feeling after washing was completed.

Example 9
Kitchen Detergent

|  |  | wt % |
|---|---|---|
| (1) | Sodium α-oleinsulfonate | 20.0 |
| (2) | POE (15 moles) alkyl ether | 8.0 |

-continued

|  | wt % |
|---|---|
| (3) Laurylamidepropyl betaine | 5.0 |
| (4) Ethanol | 1.5 |
| (5) Pigment | Appropriate amount |
| (6) Perfume | Appropriate amount |
| (7) Sodium hypotaurate salt of lauroyl hydrolyzed wheat protein | 10.0 |
| (8) Sodium glycerylsulfate laurate | 3.0 |
| (9) Purified water | Balance |

(Preparation Method)

Preparation was carried out according to the conventional method.

The kitchen detergent of the present invention exhibited a lower irritation to skin and excellent cleaning capability.

Example 10
Shampoo

|  | wt % |
|---|---|
| (1) Ethylene glycol fatty acid ester | 2.0 |
| (2) Triethanolamine hypotaurate salt of lauroyl hydrolyzed silk peptide | 10.0 |
| (3) Dodecyl maltoside | 5.0 |
| (4) Laurylsulfobetaine | 10.0 |
| (5) Diethanolamide taurate laurate | 5.0 |
| (6) Propylene glycol | 2.0 |
| (7) Coloring agent, perfume | Appropriate amount |
| (8) Purified water | Balance |

(Preparation Method)

Preparation was carried out according to the conventional method.

The shampoo of the present invention exhibited a lower irritation to hair and scalp, superior foaming properties, no stickiness and superior feeling during use.

Example 11
Shampoo

|  | wt % |
|---|---|
| (1) Sodium cocoylmethyl taurate | 8.0 |
| (2) Sodium hypotaurate salt of lauroyl hydrolyzed collagen | 20.0 |
| (3) Sodium hypotaurate salt of myristic acid | 2.0 |
| (4) Diethanol amide of coconut fatty acid | 4.0 |
| (5) Perfume | Appropriate amount |
| (6) EDTA.2Na | Appropriate amount |
| (7) Purified water | Balance |

(Preparation Method)

Preparation was carried out according to the conventional method.

The shampoo of the present invention exhibited a lower irritation to hair and scalp, superior foaming properties, no stickiness and superior feeling during use.

Example 12
Body Shampoo

|  | wt % |
|---|---|
| (1) Glycerine | 5.0 |
| (2) Potassium hypotaurate salt of palmitoyl hydrolyzed wheat protein | 5.0 |
| (3) Myristic ester of sucrose | 1.0 |
| (4) Potassium N-methyltaurate laurate | 10.0 |
| (5) Sodium laurylsulfonsuccinate | 5.0 |
| (6) Diethanol amide of coconut oil | 3.0 |
| (7) Chelating agent | 0.1 |
| (8) Coloring agent, perfume | Appropriate amount |
| (9) Purified water | Balance |

(Preparation Method)

Preparation was carried out according to the conventional method.

The body shampoo of the present invention exhibited a lower irritation to skin, excellent foaming during use, and a moist feeling after washing was completed.

Example 13
Body Shampoo

|  | wt % |
|---|---|
| (1) Sorbitol | 2.0 |
| (2) Erythritol | 5.0 |
| (3) Potassium N-methyltaurate α-hydroxylaurate | 15.0 |
| (4) Sodium hypotaurate salt of stearoyl hydrolyzed soybean protein | 5.0 |
| (5) Diethanol amide of coconut oil | 3.0 |
| (6) Chelating agent | 0.1 |
| (7) Cationized cellulose | 0.2 |
| (8) Coloring agent, perfume | Appropriate amount |
| (9) Purified water | Balance |

(Preparation Method)

Preparation was carried out according to the conventional method.

The body shampoo of the present invention exhibited a lower irritation to skin, excellent foaming during use, and a moist feeling after washing was completed.

Example 14
Liquid Detergent for Clothes

|  | wt % |
|---|---|
| (1) Sodium POE (3 moles) lauryl ether sulfate | 10.0 |
| (2) Maltotritol hydroxydodecyl ether | 30.0 |
| (3) Lysine hypotaurate salt of lauroyl hydrolyzed collagen | 15.0 |
| (4) Distearyldimethyl ammonium chloride | 2.0 |
| (5) Sodium taurate hydroxylauryl ether carboxylate | 0.5 |
| (6) Bleach | Appropriate amount |
| (7) Purified water | Balance |

(Preparation Method)

Preparation was carried out according to the conventional method.

The detergent for clothes of the present invention was highly safe and had a superior cleaning capability.

Example 15
Powder Detergent for Clothes

|   | wt % |
|---|---|
| (1) LAS-Na | 15.0 |
| (2) Sodium hypotaurate salt of lauroyl hydrolyzed soybean protein | 1.0 |
| (3) Sodium hypotaurate salt of myristic acid | 3.0 |
| (4) $Na_2SO_4$ | 30.0 |
| (5) 2-phenylacetamide | 2.0 |
| (6) CMC (66%) | 1.5 |
| (7) Metasilicic soda (anhydride) | 20.0 |
| (8) Fluorescent whitening agent | 0.2 |
| (9) $Na_2CO_3$ | Balance |

(Preparation Method)

Preparation was carried out according to the conventional method.

The powder detergent for clothes of the present invention was highly safe and had a superior cleaning capability.

Example 16
Solid Soap

|   | wt % |
|---|---|
| (1) Beef tallow | 20.0 |
| (2) Coconut oil | 12.0 |
| (3) Castor oil | 5.0 |
| (4) Olive oil | 3.0 |
| (5) Sodium taurate | 6.0 |
| (6) Ethanol | 20.0 |
| (7) Maltitolhydroxyhexadecyl ether | 4.0 |
| (8) Sodium hypotaurate salt of isostearoyl hydrolyzed soybean protein | 1.0 |
| (9) Glycerine | 5.0 |
| (10) Sucrose | 10.0 |
| (11) Cyclohexylguanidine | 3.0 |
| (12) EDTA | 0.1 |
| (13) Perfume | Appropriate amount |
| (14) Pigment | Appropriate amount |
| (15) Purified water | Balance |

(Preparation Method)

Preparation was carried out according to the conventional method.

The solid soap of the present invention exhibited a lower irritation to skin, excellent foaming during use, and a refreshing feeling after washing was completed.

Example 17
Liquid Soap

|   | wt % |
|---|---|
| (1) Lauric acid | 3.0 |
| (2) Myristic acid | 7.0 |
| (3) Palmitic acid | 3.0 |
| (4) Oleic acid | 2.5 |
| (5) Lauroyldiethanolamide | 6.0 |
| (6) Propylene glycol | 11.0 |
| (7) Erythritol | 4.0 |
| (8) Sodium hypotaurate salt of lauroyl hydrolyzed collagen | 10.0 |
| (9) Triethanolamine taurate laurate | 3.0 |
| (10) Sucrose | 5.0 |
| (11) Sodium N-methyltaurate | 3.0 |
| (12) EDTA | 0.1 |
| (13) p-aminobenzamidine | 1.0 |
| (14) Perfume | Appropriate amount |
| (15) Purified water | Balance |

(Preparation Method)

Preparation was carried out according to the conventional method.

The liquid soap of the present invention exhibited a lower irritation to skin, excellent foaming during use, and a refreshing feeling after washing was completed.

Example 18
Kitchen Detergent

|   | wt % |
|---|---|
| (1) Sodium α-oleinsulfonate | 20.0 |
| (2) POE (15 moles) alkyl ether | 8.0 |
| (3) Laurylamidepropyl betaine | 5.0 |
| (4) Ethanol | 1.5 |
| (5) Pigment | Appropriate amount |
| (6) Perfume | Appropriate amount |
| (7) Sodium hypotaurate salt of lauroyl hydrolyzed wheat protein | 10.0 |
| (8) Sodium glycerylsulfate laurate | 3.0 |
| (9) Purified water | Balance |

(Preparation Method)

Preparation was carried out according to the conventional method.

The kitchen detergent of the present invention exhibited a lower irritation to skin and excellent cleaning capability.

What is claimed is:

1. A detergent composition which contains an alkali metal taurate salt of a fatty acid represented by the following general formula [Chemical formula 45]

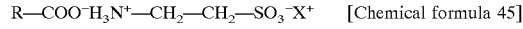

R—COO⁻H₃N⁺—CH₂—CH₂—SO₃⁻X⁺    [Chemical formula 45]

(In this formula, R denotes a saturated or unsaturated hydrocarbon group with a carbon number of 7–23 and X denotes an alkali metal).

2. A detergent composition which contains an organic alkali taurate salt of a fatty acid represented by the following general formula [Chemical formula 46]

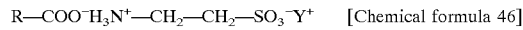

R—COO⁻H₃N⁺—CH₂—CH₂—SO₃⁻Y⁺    [Chemical formula 46]

(In this formula, R denotes a saturated or unsaturated hydrocarbon group with a carbon number of 7–23 and Y denotes an organic alkali).

3. A surfactant consisting of an organic alkali taurate salt of a fatty acid represented by the following general formula [Chemical formula 48]

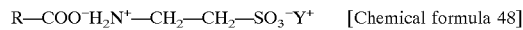

R—COO⁻H₂N⁺—CH₂—CH₂—SO₃⁻Y⁺    [Chemical formula 48]

(In this formula, R denotes a saturated or unsaturated hydrocarbon group with a carbon number of 7–23 and Y denotes an organic alkali).

4. A detergent composition which contains one or more hydroxy fatty acid salts of an (a) organic alkali taurate, (b) organic alkali N-methyltaurate, (c) organic alkali hypotaurate, (d) alkali metal taurate, (e) alkali metal N-methyltaurate, and/or an alkali metal hypotaurate.

5. The detergent composition of claim 4 wherein the hydroxy fatty acid salt is represented by any of the following Chemical formulas 53–54 as follows:

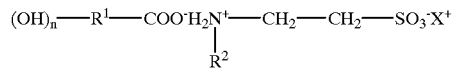  Chemical formula 53

(In this formula, $R^1$ denotes a saturated or unsaturated hydrocarbon group with a carbon number 7–23, $R^2$ denotes a methyl group or hydrogen, X denotes a alkali metal or organic alkali and n denotes an inter 1–2)

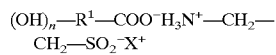  Chemical formula 54

(In this formula, $R^1$ denotes a saturated or unsaturated hydrocarbon group with a carbon number of 7–23, X denotes an alkali metal or organic alkali and n denotes an integer 1–2).

6. A hydroxy fatty acid salt of any of an (a) alkali metal taurate, (b) alkali metal N-methyltaurate, (c) alkali metal hypotaurate, (d) organic alkali taurate, (e) organic alkali N-methyltaurate, and (f) an organic alkali hypotaurate.

* * * * *